United States Patent
Matray et al.

(10) Patent No.: US 6,649,351 B2
(45) Date of Patent: *Nov. 18, 2003

(54) METHODS FOR DETECTING A PLURALITY OF ANALYTES BY MASS SPECTROMETRY

(75) Inventors: Tracy J. Matray, Campbell, CA (US); Vincent S. Hernandez, Brookdale, CA (US); Ahmed Chenna, Sunnyvale, CA (US); Herbert Hooper, Wellesley, MA (US); Sharat Singh, San Jose, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 69 days.

This patent is subject to a terminal disclaimer.

(21) Appl. No.: 10/008,593

(22) Filed: Nov. 9, 2001

(65) Prior Publication Data

US 2002/0150927 A1 Oct. 17, 2002

Related U.S. Application Data

(63) Continuation-in-part of application No. 09/698,846, filed on Oct. 27, 2000, which is a continuation-in-part of application No. 09/602,586, filed on Jun. 21, 2000, now Pat. No. 6,514,700, which is a continuation-in-part of application No. 09/561,579, filed on Apr. 28, 2000, now abandoned, which is a continuation-in-part of application No. 09/303,029, filed on Apr. 30, 1999, now Pat. No. 6,322,980.

(51) Int. Cl.[7] .................. C12Q 1/68; C12M 1/36; C07H 21/04; C07H 21/02; C07H 19/04
(52) U.S. Cl. ............... 435/6; 435/287.2; 536/23.1; 536/24.3; 536/25.4; 536/26.6
(58) Field of Search .................. 435/6, 287.2; 536/23.1, 536/24.3, 25.4, 26.6

(56) References Cited

U.S. PATENT DOCUMENTS

| | | | | |
|---|---|---|---|---|
| 4,331,590 A | 5/1982 | Bocuslaski | ............... | 260/112 B |
| 4,650,750 A | 3/1987 | Giese | ............... | 435/7 |
| 4,709,016 A | 11/1987 | Giese | ............... | 530/389 |
| 4,780,421 A | 10/1988 | Kameda | ............... | 436/518 |
| 5,360,819 A | 11/1994 | Giese | ............... | 514/538 |
| 5,516,636 A | 5/1996 | McCapra | ............... | 435/6 |
| 5,516,931 A | 5/1996 | Giese | ............... | 560/59 |
| 5,565,324 A | 10/1996 | Still | ............... | 435/6 |
| 5,602,273 A | 2/1997 | Giese | ............... | 560/60 |
| 5,604,104 A | 2/1997 | Giese | ............... | 435/7.1 |
| 5,610,020 A | 3/1997 | Giese | ............... | 435/7.1 |
| 5,622,929 A | 4/1997 | Willner | ............... | 514/8 |
| 5,650,270 A | 7/1997 | Giese | ............... | 435/6 |
| 5,705,622 A | 1/1998 | McCapra | ............... | 536/23.1 |
| 5,709,994 A | 1/1998 | Pease | ............... | 435/4 |
| 5,721,099 A | 2/1998 | Still | ............... | 435/6 |
| 5,756,726 A | 5/1998 | Hemmi | ............... | 540/474 |
| 5,777,096 A | 7/1998 | Grossman | ............... | 536/24.3 |
| 5,789,172 A | 8/1998 | Still | ............... | 435/6 |
| 5,807,675 A | 9/1998 | Davalian | ............... | 435/6 |
| 5,843,666 A | 12/1998 | Akhavan-Tafti | ............... | 435/6 |
| 5,846,839 A | 12/1998 | Gallop | ............... | 436/518 |
| 5,952,654 A | 9/1999 | Giese | ............... | 250/288 |
| 6,027,890 A | * | 2/2000 | Ness et al. | ............... | 435/6 |
| 6,312,893 B1 | 11/2001 | Van Ness | ............... | 435/6 |

OTHER PUBLICATIONS

Adam et al., "Photooxygenation (Singlet Oxygen) of Tetrathioethylenes", Journal of the American Chemical Society, vol. 94:4, 1972, pp. 1206–1208.

Adam et al., "Photooxygenation of Vinyl Sulfides: Substituent Effects on the [2+2] Cycloaddition versus Schenck Ene Reaction Modes", Tetrahedron Letters, vol. 36, No. 43, Pergamon Press 1995, pp. 7853–7854.

Ando et al., "Photosensitized Oxygenation of Vinylic Sulphides", J.C.S. Chem. Comm., 1972, pp. 477–478.

Ando et al., "Singlet Oxygen Reaction—II Alkylthiosubstituted Ethylene[1]", Tetrahedron, vol. 29, Pergamon Press 1973, pp. 1507–1513.

Ando et al., "Singlet Oxygen Reaction. III. Solvent and Temperature Effects on the Photosensitized Oxygenation of Vinyl Sulfides and Vinyl Ethers", Journal of the American Chemical Society, vol. 96:21, 1974, pp. 6766–6768.

Ando et al., "Singlet Oxygen Reaction. IV. Photooxygenation of Enamines Involving a Two–Step Cleavage of a 1, 2–Dioxetane Intermediate[1]", Journal of American Chemical Society, vol. 97:17, 1975, pp 5028–5029.

Ando et al., "Singlet Oxygen Reaction V. Ring Size Effects on the Decomposition of Sulfur Substituted 1,2–Dioxetane[1]", Tetrahedron Letters, No. 47, Pergamon Press 1975, pp. 4127–4130.

Fitch et al., "Improved Methods for Encoding and Decoding Dialkylamine–Encoded Combinatorial Libraries", J. Comb. Chem., *1*, 1999, pp. 188–194.

Giese, "Electrophoric Release Tags: Ultrasensitive Molecular Labels Providing Multiplicity", Trends in Analytical Chemistry, vol. 2, No. 7, 1983, pp. 166–168.

Haff et al., "Multiplex Genotyping of PCR Products with Mass Tag–Labled Primers", Nucleic Acids Research, vol. 25, No. 18, 1997, pp. 3749–3750.

(List continued on next page.)

*Primary Examiner*—Ethan Whisenant
*Assistant Examiner*—J. Tung
(74) *Attorney, Agent, or Firm*—Stephen C. Macevicz

(57) ABSTRACT

The invention provides a method for detecting a target analyte, by: (a) contacting one or more target analytes with a set of first and second binding reagents under conditions sufficient for binding of a target analyte with the first and second binding reagents, each of the first binding reagents containing a cleavage-inducing moiety and a target binding moiety, each of the second binding reagents containing a tagged probe having a mass modifier region attached to a target binding moiety by a cleavable linkage, the cleavable linkage being susceptible to cleavage when in proximity to an activated cleavage-inducing moiety; (b) activating the cleavage-inducing moiety to release a tag reporter, and (c) detecting a mass of the tag reporter, the mass uniquely corresponding to a known target analyte.

19 Claims, 4 Drawing Sheets

OTHER PUBLICATIONS

Holland et al., "Detection of Specific Polymerase Chain Reaction Product by Utilizing the 5'→3'Exonuclease Activity of *Thermus Aquaticus* DNA Polymerase", Proc. Natl. Acad. Sci. USA, vol. 88, 1991, pp. 7276–7280.

Kochevar et al., "Photosensitized Production of Singlet Oxygen", Methods in Enzymology, vol. 319, 2000, pp. 20–29.

Rakestraw et al., "Antibody–Targeted photolysis: In vitro Studies with Sn(IV) Chlorin e6 Covalently Bound to Monoclonal Antibodies Using a Modified Dextran Carrier", Proc. Natl. Acad. Sci. USA, vol. 87, 1990, pp. 4217–4221.

Strong,"Antibody–Targeted Photolysis", Annals New York Academy of Sciences, vol. 745, 1994, pp. 297–320.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426–5430.

Yarmush et al., "Antibody Targeted Photolysis", Critical Reviews in Therapeutic Drug Carrier Systems, vol. 10, 1993, pp. 197–252.

Griffin et al, "Genetic Identification by Mass Spectrometric Analysis of Single–Nucleotide Polymorphisms: Ternary Encoding of Genotypes", Anal Chem, 72, 3298–3302 (2000).

Linxiao Xu et al, "Electrophore Mass Tag Dideoxy DNA Sequencing", Anal Chem, 88, 3595–3602, (1997).

Nanying Bian et al, "Detection Via Laser Desorption and Mass Spectrometry of Multiplex Electrophore–labled Albumin", Rapid Communications in Mass Spectrometry, vol. 11, 1781–1784, (1997).

* cited by examiner

METHODS FOR DETECTING A PLURALITY OF ANALYTES BY MASS SPECTROMETRY

This application is a continuation in part of Ser. No. 09/698,846, filed Oct. 27, 2000, which is a continuation in part of Ser. No. 09/602,586 filed Jun. 21, 2000, now U.S. Pat. No. 6,514,700, which is a continuation in part of Ser. No. 09/561,579 filed Apr. 28, 2000, now abandoned, which is a continuation in part of Ser. No. 09/303,029 filed Apr. 30, 1999, now U.S. Pat. No. 6,322,980.

BACKGROUND OF THE INVENTION

This invention relates generally to the field of genome and proteome analysis and, more specifically to methods for detecting multiple analytes using mass spectrometry.

Molecular assays have been developed that can identify and quantitate a single analyte, such as a nucleic acid or protein, in a biological sample. These assays can be used, for example, to detect a known mutation in a gene, an infectious agent, or a protein associated with a disease such as cancer. The need to identify and quantitate many analytes from the same sample has become increasingly apparent in many branches of medicine. For example, it can be desirable to analyze a single sample for the presence of several infectious agents at once, for several genes that are involved in a particular disease, or for several genes that are involved in different diseases.

The full sequencing of the human genome has facilitated methods for comparing all of the genes between different cells or individuals. Different individuals are known to contain single base pair changes, called single nucleotide polymorphisms (SNPs), throughout their genomes. It is believed that there will be about one polymorphism per 1,000 bases, resulting in a large number of differences between individuals. These single nucleotide differences between individuals can result in a wide variety of physiological consequences. For example, the presence of different SNPs in cytochrome P450 genes can predict the ability or inability to metabolize certain drugs. Screening individuals for the presence of multiple SNPs could be used to predict how an individual will respond to a particular drug or treatment.

DNA microarrays are devices that contain thousands of immobilized DNA sequences on a miniaturized surface. Arrays have made the process of detecting several genes from a single sample more efficient. Unfortunately, despite the miniaturization of microarray formats, this method still requires significant amounts of the biological sample. In addition, in microarray methods there is a trade-off between high dynamic range and high sensitivity so that in order to increase dynamic range to detect genes of various abundance levels, there is a concomitant decrease in sensitivity.

Proteomics is the study of proteins expressed in a cell. Although more complex than genomics, proteomic analysis can give a more accurate picture of the state of a cell than genomic analysis. For example, the level of mRNA transcribed from a gene does not always correlate to the level of expressed protein. Therefore, analysis of gene expression alone does not always give an accurate picture of the amount of protein derived from a gene of interest. In addition, many proteins are post-translationally modified and these modifications are often important for activity. The type and level of modification of a protein can not be accurately predicted using genome analysis. Therefore, it is important to study a cell in terms of the proteins that are present. For example, it can be desirable to identify and quantitate all proteins present in a cell from an individual and compare the profile with other cells from the same or different individuals.

Assays for the detection of single proteins using antibody-based assays are available. However, analysis of several proteins simultaneously in the same sample can be more difficult. Two-dimensional gel electrophoresis has been used to study the protein content of a cell. This technique requires an individual gel for each sample and sophisticated software to compare the pattern of protein spots between gels. In addition, it is difficult to detect low abundance proteins using this method and several proteins, such as membrane proteins or proteins of very low or high molecular weight, are not ameable to the analysis.

Another aspect of proteome analysis is the study of protein-protein interactions within a cell. These protein-protein interactions form the basis of biochemical pathways within the cell. Two-hybrid assays have been used to study individual protein-protein interactions. However, this assay requires the cloning of the gene for a protein of interest into expression vectors, which is a labor-intensive process. In addition, two-hybrid assays often have a high rate of false positives where the protein of interest non-specifically interacts with another protein. Furthermore, two hybrid assays require several days to perform due to the growth cycle of the cells explored, which limits the number of assays can be performed at one time.

Thus, there exists a need for methods to identify and quantitate a plurality of analytes, including nucleic acids and proteins, quickly and with high sensitivity, high accuracy, and a large dynamic range. The present invention satisfies this need and provides related advantages as well.

SUMMARY OF THE INVENTION

The invention provides a method for detecting a target nucleic acid sequence, by: (a) contacting one or more target nucleic acid sequences with a set of tagged probes under conditions sufficient for hybridization of a target nucleic acid sequence with a tagged probe, the tagged probes containing a mass modifier region attached to a nucleic acid target binding moiety by a bond that is cleavable by a nuclease, the nucleic acid target binding moiety containing at least one bond resistant to the nuclease; (b) treating the tagged probe hybridized to the target nucleic acid with a nuclease under conditions sufficient for cleavage of the nuclease-cleavable bond to release a tag reporter, and (c) detecting a mass of the tag reporter, the mass uniquely corresponding to a known target sequence.

The invention also provides a method for detecting a target analyte, by: (a) contacting one or more target analytes with a set of tagged probes attached to a cleavage-inducing moiety under conditions sufficient for binding of a target analyte with a tagged probe, the tagged probes containing a mass modifier region attached to a target binding moiety by a cleavable linkage, the cleavable linkage being susceptible to cleavage when the cleavage-inducing moiety is activated by visible light; (b) separating tagged probes bound to a target binding moiety from unbound tagged probes; (c) activating the cleavage-inducing moiety with visible light to release a tag reporter, and (d) detecting a mass of the tag reporter, the mass uniquely corresponding to a known target analyte.

The invention further provides a method for detecting a target analyte, by: (a) contacting one or more target analytes with a set of first and second binding reagents under conditions sufficient for binding of a target analyte with the first and second binding reagents, each of the first binding reagents containing a cleavage-inducing moiety and a target binding moiety, each of the second binding reagents containing a tagged probe having a mass modifier region attached to a target binding moiety by a cleavable linkage, the cleavable linkage being susceptible to cleavage when in proximity to an activated cleavage-inducing moiety; (b) activating the cleavage-inducing moiety to release a tag reporter, and (c) detecting a mass of the tag reporter, the mass uniquely corresponding to a known target analyte.

The invention also provides a method for identifying a binding partner of a specific binding pair, by: (a) incorporating a cleavage-inducing moiety into a first binding partner of a specific binding pair; (b) contacting the first binding partner having an incorporated cleavage-inducing moiety with a set of second binding partners under conditions sufficient for binding, each of the second binding partners containing a tagged probe having a mass modifier region attached to a target binding moiety by a cleavable linkage, the cleavable linkage being susceptible to cleavage when in proximity to an activated cleavage-inducing moiety; (c) activating the cleavage-inducing moiety to release a tag reporter, and(d) detecting a mass of the tag reporter, the mass uniquely corresponding to a known second binding partner of a specific binding pair.

DETAILED DESCRIPTION OF THE INVENTION

Figure 1:
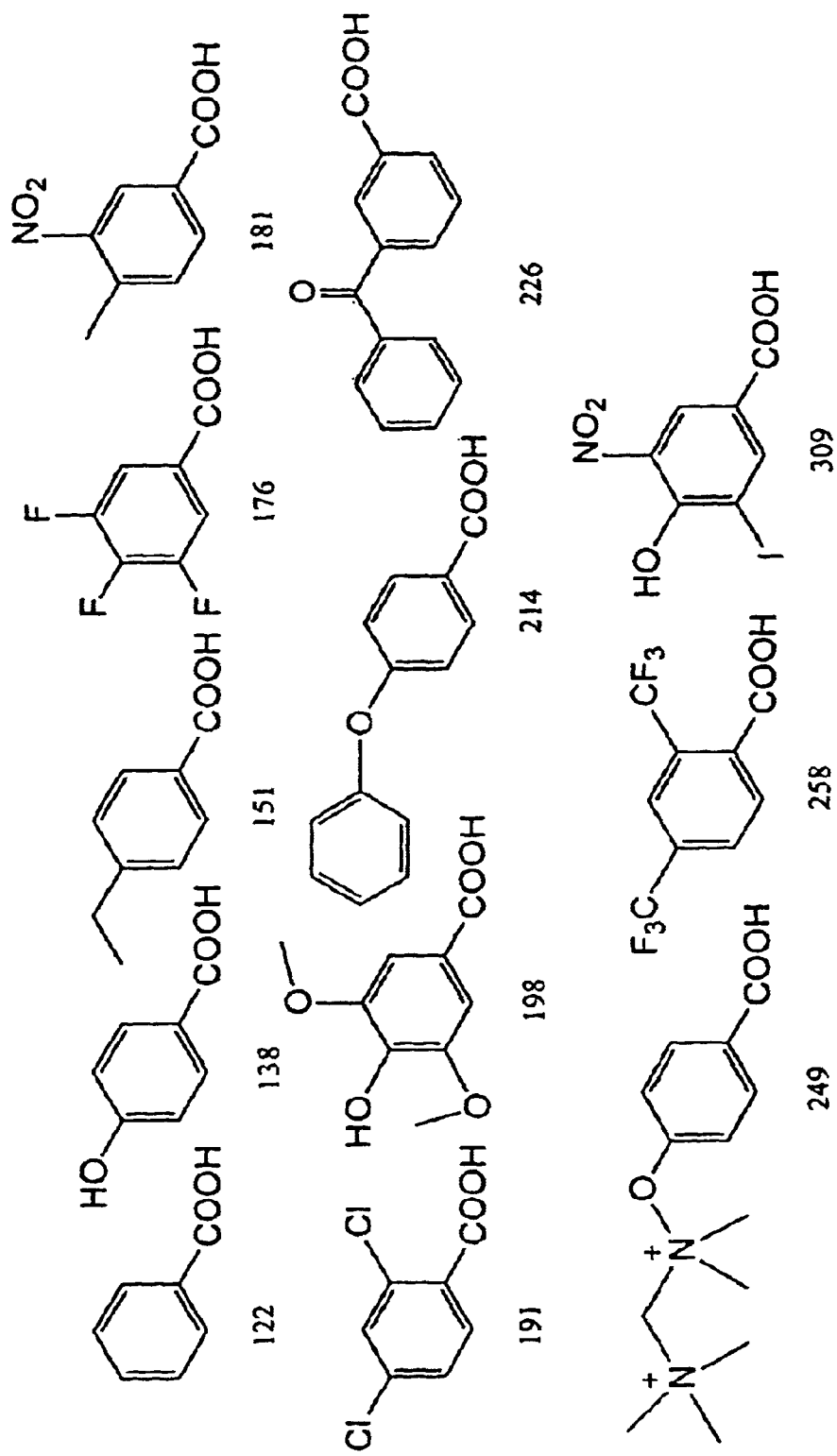
FIG. 1 shows the structures of several benzoic acid derivatives that can serve as mobility or mass modifiers.

This invention is directed to methods for the detection of a wide variety of different analytes in a sample. The present invention employs tagged probes that are separately detectable based on a unique physical characteristic, such as a unique mass. The tagged probes can be bound to different analytes and released upon specific binding events for simultaneous detection of multiple different analytes in a single sample. For example, large sets of tagged probes with different masses can be generated in order to detect several analytes simultaneously in one assay. After binding the analyte, the complexes are treated with reagents which cleave off the releasable portion, called a tag reporter. The presence of the released tag reporter can be detected and is indicative of the presence and amount of the analyte in the sample. Detection of the tag reporter using mass spectrometry can enhance the sensitivity, accuracy, dynamic range, and degree of multiplexing of analyte assays.

In one embodiment, the invention provides a method of detecting a target analyte by contacting one or more target analytes with a set of first and second binding reagents. Each of the first binding reagents contains a cleavage-inducing moiety and each of the second reagents contains a tagged probe having a mass modifier region attached to a target-binding moiety by a cleavable linkage. The cleavable linkage is susceptible to cleavage when in proximity to an acitivated cleavage-inducing moiety. A binding event between first and second bound reagents, either directly or indirectly to the same analyte is sufficient to bring the linkage and cleavage-inducing moiety in close proximity to result in cleavage and release of the corresponding tag reporter upon activation. The mass of the tag reporter is detected and will uniquely identify the target analyte from which it was bound.

Throughout this disclosure several terms have been used interchangeable to describe the same component. For example, "tag reporter", "electrophoresis tag reporter", and "e-tag reporter" all refer to the same component. These synonymous terms are listed in the definitions below and it is understood that any of the synonymous terms can be used to describe the component.

In defining the terms below, it is useful to consider the makeup of the "tagged probe" also called "electrophoretic probe," or "e-tag probe," as used in practicing the methods of the invention. A probe has four basic components or moieties: (i) an optional detection group or moiety, D (ii) a mobility or mass modifier, M (iii) a target-binding moiety, T, and (iv) a linking group, L, that links the mobility or mass modifier and detection group, if used, to the target-binding moiety. A tagged probe does not require a specialized detection group when the released tag reporter will be detected using mass spectrometry. These terms will first be examined in the context of the functioning of the tagged or electrophoretic probes in the invention, then more fully defined by their structural features.

The function of a tagged or an electrophoretic probe in the invention is first to interact with a target, such as a single-stranded nucleic acid, a ligand-binding agent, such as an antibody or receptor, or an enzyme, e.g., as an enzyme substrate. The portion or region of the probe that binds to the target is the "target-binding moiety," abbreviated "T." After the target-binding moiety of a tagged or an e-tag probe binds to a target, the linking group of the tagged or electrophoretic probe can be cleaved to release a "tag reporter" or an "e-tag reporter" that has a unique mass-to-charge or charge-to-mass ratio and thus a unique electrophoretic mobility in a defined electrophoretic system or a unique mass as determined in a mass spectrometry system. A tag reporter is sometimes referred to as having a unique mass-to-charge ratio or sometimes as having a unique charge-to-mass ratio. Since both mass and charge are known in this ratio, and one value is the inverse of the other, these terms can be used interchangeably to describe the mass and charge characteristics of a tag reporter. The tag reporter or e-tag reporter is composed of the detection group, if used, mobility or mass modifier, and any residue of the linking group that remains associated with the released tag reporter or e-tag reporter after cleavage. Therefore, the second function of the tagged probe or electrophoretic probe is to release a tag reporter or an e-tag reporter, which can be identified according to its unique and known electrophoretic mobility or mass.

According to an important feature of the invention, there is provided a set of tagged probes or electrophoretic probes, each of which has a unique target-binding moiety and an associated "tag moiety" or "e-tag moiety" that imparts to the associated tag reporter or e-tag reporter a unique mass or electrophoretic mobility by virtue of a unique charge-to-mass ratio. In general, the unique charge-to-mass ratio of a tag moiety or an e-tag moiety is due to the chemical structure of the mobility or mass modifier, since the detection group, if used, and linking-group residue (if any) will be common to any set of tagged or electrophoretic probes. However, it is recognized that the detection group can make unique charge and/or mass contributions to the tag reporters or e-tag reporters as well. For example, a set of tagged probes or electrophoretic probes may be made up of a first subset having a group of mobility or mass modifiers which impart unique electrophoretic mobilities or masses to the subset in combination with a detection group having one defined charge and/or mass, and a second subset having the same group of mobility or mass modifiers in combination with a second detection group with a different charge and/or mass, thus to impart electrophoretic mobilities or masses which are unique among both subsets.

The different target-binding moieties in a set of tagged probes or electrophoretic probes are typically designated "$T_j$", where the set of probes contains n members, and each $T_j$, where j=1 to n, is different. Therefore, each target binding moiety can bind specifically and/or with unique affinities to different targets. A set of tagged probes or electrophoretic probes of the invention includes at least about 2 members, generally at least about 5 members, and more generally at least about 10–100 or 100 or more members. Therefore, it can range, for example, from at least about 2 or more to greater than 100.

A "detection group," abbreviated "D," refers to a chemical group or moiety that is capable of being detected by a suitable detection system, or alternatively a chemical group providing means for generating a detection group. Means for generating a detection group may include either incorporation of a reactive group to form a bond with a detectable moiety, or the detection group may be a catalytic moiety capable of catalyzing synthesis of a detection group in an electrophoretic system. A preferred embodiment of a detection system is in the context of detecting molecules during or after electrophoretic separation. A tagged probe does not require a specialized detection group when the released tag reporter will be detected using mass spectrometry or electrophoresis. However, a detection group can be used to add mass to the released tag reporter for mass spectrometry analysis or for ease of detection for electrophoresis analysis. One preferred detection group is a fluorescent moiety or other chromogenic moiety that can be readily detected during or after electrophoretic separation of molecules by illuminating the molecules with a light source in the excitation wavelength and detecting fluorescence emission from the irradiated molecules. Exemplary fluorescent moieties will be given below. In addition to a fluorophore, a detection component of a tagged probe can be, for example, a chromophore or an electrochemical compound capable of a detectable reaction in the presence of a redox agent. As noted above, the detection group is typically common among a set or subset of different tagged probes or e-tag probes, but may also differ among probe subsets.

Figure 2:
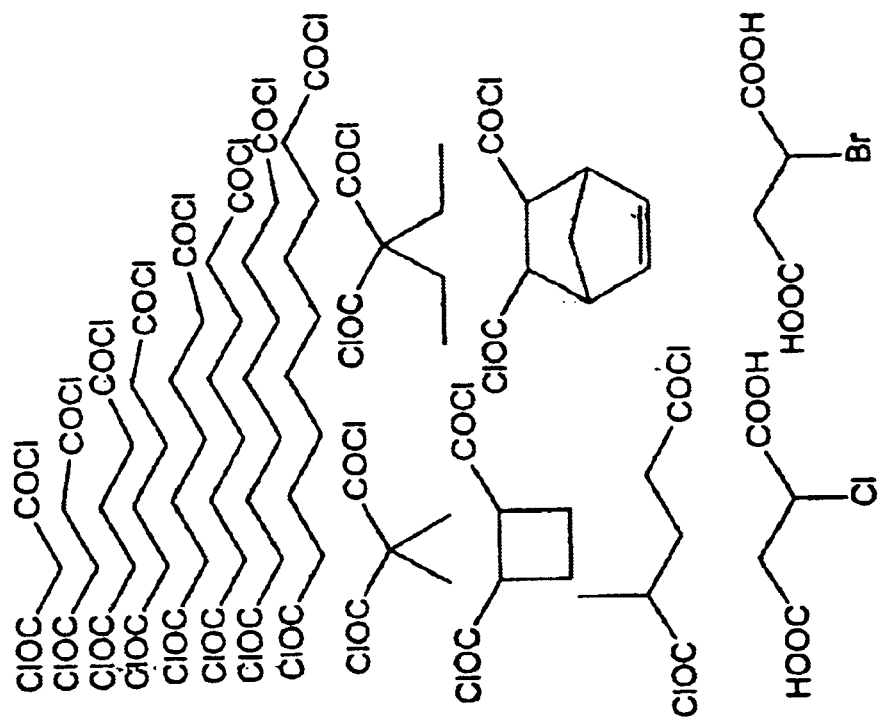
FIG. 2 shows several mobility or mass modifiers that can be used for conversion of amino dyes into tagged probe phosphoramidite monomers.
Figure 2:
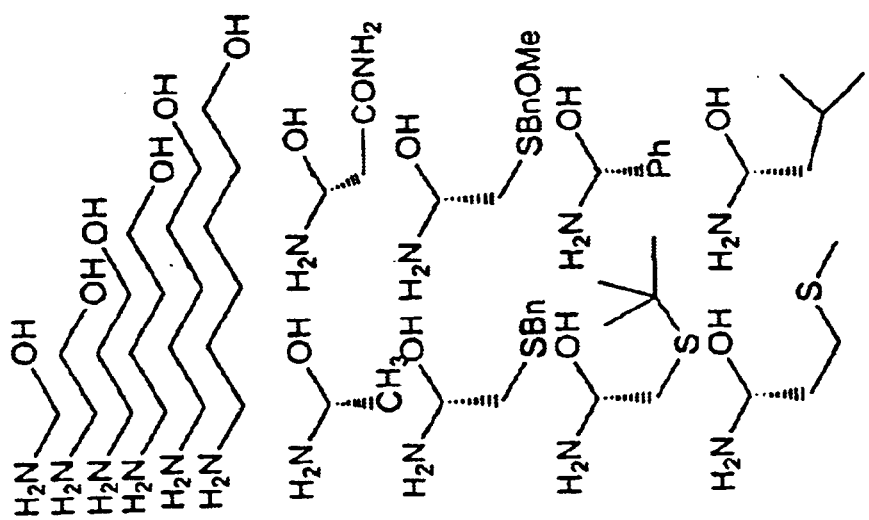

The "mobility or mass modifier," abbreviated "M," is a moiety that confers upon the probe or reporter molecule containing it, a "separation characteristic" that allows separation of each probe or reporter molecule from all other probes and reporters of a designated set. The type of separation characteristic used will typically be determined by the separation platform being employed for analysis of an assay. In one preferred embodiment, M is a generally a moiety designed to have a particular charge to mass ratio, and thus a particular electrophoretic mobility in a defined electrophoretic system. In another preferred embodiment, M will be a moiety characterized by a unique mass, allowing specific identification in a mass-based separation, e.g., by mass spectrometry. Exemplary types of mobility or mass modifiers are discussed below. In a set of n tagged probes or electrophoretic probes, each unique mobility or mass modifier is designated $M_j$, where j=1 to n, as above. The mobility or mass modifier may be considered to include a mass-modifying region and/or a charge-modifying region or a single region that acts as both a mass- and charge-modifying region. Also since a charge group has a mass, a charge can be used to alter the mass of the mobility or mass modifier region. FIGS. 1 and 2 depict the structures of several benzoic acid derivatives that can serve as mobility or mass modifieres, and several mobility or mass modifiers that can be used for conversin of amino dyes into tagged probe or tag phosphoramidite monomers.

The detection group, if used, and mobility or mass modifier in the tagged probe or electrophoretic probe form a "tag moiety" or an "e-tag moiety" which is linked to the target-binding moiety by a "linking group" which may be only a covalent bond which is cleavable under selected cleaving conditions, or a chemical moiety or chain, such as a nucleotide and associated phosphodiester bond, an oligonucleotide with an internal cleavable bond, an oligopeptide, or an enzyme substrate, that contains a cleavable chemical bond. Cleavage typically occurs as the result of binding of the probe to the target, which is followed by enzyme or catalyzed cleavage of the linking-group bond.

The linking group may or may not contribute a linking-group "residue" to the released tag reporter or e-tag reporter, also dependent on the nature of the linking group and the site of cleavage. For example, where the linking group is a covalent bond, or cleavage of the linking group occurs immediately adjacent the "tag moiety" or "e-tag moiety," the linking group will leave no residue, i.e., will not contribute additional mass and charge to the released tag reporter or e-tag reporter. Similarly, where the linking group is a chemical group or chain which is cleaved internally or immediately adjacent the target-binding moiety, cleavage of the linking group will leave a residual mass and, possible charge contribution to the released tag reporter or e-tag reporter. In general, this contribution will be relatively small, and will be the same for each different tag reporter or e-tag reporter (assuming a common linking group within the probe set). As such, the residue will not effect the relative electrophoretic mobilities or masses of the released tag reporter or e-tag reporters, nor the ability to resolve the tag reporter or e-tag reporters into mass or electrophoretic species that can be uniquely identified.

The following definitions are to be understood in the context of the above function of the various components of tagged probes or electrophoretic probes and tag reporters or e-tag reporters. In some case, structure designations based on different lettering schemes are employed, and the equivalency between or among structures with different lettering schemes will be understood by those skilled in the art, in view of the intended function of the structure being referred to.

An electrophoretically tagged probe, or "e-tag probe," or "tagged probe" refers to one of a set of probes of the type described above having unique target-binding moieties and associated tag moieties or e-tag moieties. The probes are described herein by the following form (D, $M_j$)-L-$T_j$, or $M_j$-L-$T_j$, wherein according to this terminology, a set of probes will contain n members, where j=1 to n, the detection group is represented by D, $M_j$ is the jth mobility or mass modifier, $T_j$ is the jth target-binding moiety, and the linking group is represented by L. In this structural designation, (D, $M_j$) intends that either the detection group or the mobility or mass modifier may be the moiety joined to the linking group, i.e., both D-$M_j$-L-$T_j$ and $M_j$-D-L-$T_j$ are contemplated.

A "set," "group" or "library" of tagged probes or electrophoretic probes refers to a plurality of tagged probes or e-tag probes of typically at least five, typically 10–100 or 100 or more probes, each with a unique target-binding moiety and associated tag moiety or e-tag moiety. As used herein, the term "tagged probe set" or "electrophoretic tag probe set" or "e-tag probe set" refers to a set of probes for use in detecting each or any of a plurality of known, selected targets, or for detecting the binding of, or interaction between, each or any of a plurality of ligands and one or more target antiligands.

The term "target-binding moiety" or "T" refers to the component of a tagged probe or an e-tag probe that participates in recognition and specific binding to a designated target. The target-binding moiety may also be defined based on the type of target, e.g., as a SNP detection sequence. In one general embodiment of the target-binding moiety for use in detection of nucleic acid targets, T is an oligonucleotide target-binding moiety. In such cases, T has a sequence of nucleotides U connected by intersubunit linkages:

$$U_1 = U_2 = U_3 = U_4 = U_5 = U_6 = U_i$$

where = corresponds to intersubunit linkages $B_{i,\ i+1}$, where i includes all integers from 1 to n, and n is sufficient to allow the oligonucleotide to hybridize specifically with a target nucleotide sequence. Where the target-binding moiety is an oligonucleotide, and enzyme cleavage to release a tag reporter or an e-tag reporter occurs between the first and second 5' nucleotides (between $U_1$ and $U_2$ above), the linking group and nucleotides forming the target-binding sequence can be expressed by the following representation: $U_1$ is considered the 5' nucleotide of the target-binding moiety (as in the representation above), and cleavage occurs within this moiety, that is, at a nuclease-susceptible bond between the first and the second nucleotides of the target moiety (between $U_1$ and $U_2$ above). In this representation, the bond between the first and second nucleotides ($B_{1,2}$ in the above nomenclature) is the site of cleavage, and all downstream bonds are represented by $B_{i,\ i+1}$, where i is 2 or greater. Typically the penultimate bond will be nuclease-resistant, however the target-binding moiety may include more than one nuclease-resistant linkage adjacent to the nuclease-susceptible linkage, such that cleavage of the probe will yield a single released tag reporter or e-tag reporter species. In this representation, a capture ligand, C, as described further below may be bound to the penultimate nucleotide, $U_2$.

In another exemplary representation, the 5' nucleotide is designated "N", and the nuclease-susceptible bond that links it to the 5' nucleotide (U1) of the target-binding moiety is considered as the linking group. In other words, in this representation, N and all downstream nucleotides are considered as the target-binding region. The same oligonucleotide above would now be expressed as N=U1=U2=U3=U4=U5=U6=Ui, where N is the 5' nucleotide and participates in target recognition. In this representation, a capture ligand ("C"), can be bound to the ultimate nucleotide (U1).

In another generalized embodiment for use in detection of non-nucleic acid targets, the target-binding moiety, $T_j$ is or includes a ligand capable of binding to or interacting with a target antiligand and L is a linking group connected to $T_j$ by a bond that is cleavable by a selected cleaving agent when the probe is bound to or interacting with the target antiligand. For example, a target-binding moiety can be a polypeptide that binds to another polypeptide or to a nucleic acid. Furthermore, a target-binding moiety can be a polypeptide such as an antibody, or a nucleic acid such as an aptamer.

A "tag reporter" or "electrophoretic tag" or "e-tag reporter" refers to a composition or reagent for unique identification of an entity of interest during separation. A tag reporter or an e-tag reporter has the fundamental structure given as (D, $M_j$)-L, or $M_j$-L, where D and $M_j$ are the detection group and the jth mobility or mass modifier, respectively, as defined above, and L is the linking group, and in particular, the bond or residue of the linking group remaining after cleavage. Here, enclosure of D and $M_j$ in parentheses intends that both of the structures D-$M_j$-L and $M_j$-D-L are contemplated.

For purposes of clarity, the concept of an electrophoretic tag is consistently referred to herein as "e-tag" or "tag reporter." As used herein, the term "electrophoretic tag probe" or "e-tag probe" or "tagged probe" refers to a reagent used for target recognition, which comprises an e-tag moiety or tag moiety and a target-binding moiety. Upon interaction with the corresponding target, the e-tag probe or tagged probe undergoes a change resulting in the release of an e-tag reporter or tag reporter. Such an e-tag probe or tagged probe may also be referred to as a binding member.

Tagged probes or e-tag probes of the invention find utility in performing multiplexed assays for detection/analysis of targets including, but not limited to nucleic acid detection, such as sequence recognition, SNP detection, transcription analysis or mRNA determination, allelic determination, mutation determination, HLA typing, MHC determination, and haplotype determination, in addition to detection of other ligands, such as proteins, polysaccharides, etc.

As used herein, the term "tag reporter" or "e-tag reporter" refers to the cleavage product generated as a result of the interaction between a tagged probe or an e-tag probe and its target. In one representation, a tag reporter or an e-tag reporter comprises the tag moiety or e-tag moiety plus a residual portion of the target-binding moiety ($T_j$) where, as in the nucleotide example, above, one or more nucleotides in the target-binding moiety contain the cleavable linking group. A tag reporter or an e-tag reporter resulting from the interaction of a tagged probe or an e-tag probe and a nucleic acid target typically has the 5'-end terminal nucleotide of a target-binding oligonucleotide.

In another embodiment, the tag reporter or e-tag reporter does not retain any of the target-binding moiety, but may retain a residual portion of the linking group, when the latter is considered separate from the target-binding moiety. Tag reporters or e-tag reporters can be differentiated by electrophoretic mobility or mass and are amenable to electrophoretic separation and detection, although other methods of differentiating the tags such as mass spectrometry may also find use and be preferred in several cases.

A tag reporter or an e-tag reporter resulting from the interaction of a tagged probe or an e-tag probe used to detect the binding of or interaction between a ligand and an antiligand typically has the form (D, $M_j$)-L' or $M_j$-L'. D and $M_j$ are defined above and L' is the residue of L that remains attached to (D, $M_j$) after a tag reporter or an e-tag reporter is cleaved from the corresponding tagged probe or e-tag probe.

As used herein, the term "binding event" generally refers to the binding of the target-binding moiety of a tagged probe or an e-tag probe to its target. By way of example, such binding may involve the interaction between complementary nucleotide sequences or the binding between a ligand and target antiligand. In addition, a binding event can refer to the binding of two target analytes such as occurs with a specific binding pair. For example, two polypeptides can specifically bind to each other or a small molecule can bind specifically to a polypeptide.

As used herein, the term "capture ligand", refers to a group that is typically included within the target-binding moiety or portion of a tagged probe or an e-tag probe, and is capable of binding specifically to a "capture agent" or receptor. The interaction between such a capture ligand and the corresponding capture agent may be used to separate uncleaved tagged probes or e-tag probes from released tag reporters or e-tag reporters. Uncleaved or partially cleaved tagged probes can have one or more chemical groups capable of reacting with or binding to a selected capture agent. The capture ligand can either (i) impart a mass or mobility to probes bound to the capture agent that can be used to distinguish or separate probes within a predetermined range of mass values or electrophoretic mobilities or (ii) immobilize the probes on a solid support. Distinguishing or segregating can include, for example, preventing the bound probes from being separated in a mass spectometry or migrating during electrophoresis. For example, the probe can contain a capture ligand such as biotin, which is capable of binding specifically to a capture agent such as avidin agarose beads.

As used herein, the terms "analyte," "target" or "target analyte" are intended to mean any molecule whose presence is to be detected or measured or whose function, interactions or properties are to be studied. Therefore, an analyte includes essentially any molecule for which a detectable probe or assay exists, or can be produced by one skilled in the art. For example, an analyte can be a macromolecule such as a nucleic acid, sugar, polysaccharide, lipid, polypeptide or carbohydrate, or an analyte can be a small molecule compound. The presence or absence of an analyte can be measured quantitativly or qualitativly. Analytes can come in a variety of different forms including, for example, simple or complex mixtures, or in substationally purified forms. For example, an analyte can be part of a sample that contains other components or can be the sole or major component of the sample. Therefore, an analyte can be a component of a whole cell or tissue, a cell or tissue extract, a fractionated lysate thereof or a substantially purified molecule. Also an analyte can have either a known or unknown sequence or structure.

Analytes can be monovalent (monoepitopic) or polyvalent (polyepitopic), for example, monovalent analytes include drugs, metabolites, enzyme substrates, enzyme inhibitors, low molecular weight peptides, pesticides, pollutants, and the like. These analytes can generally be from about 100 daltons (D) to about 2,000 D molecular weight, more usually from about 125 D to about 1,000 D molecular weight. However monovalent analytes can also be smaller than 100 D or larger than 1000 D. Polyvalent analytes can include nucleic acids, for example, m-RNA, r-RNA, t-RNA, DNA, DNA-RNA duplexes as well as other forms of nucleic acids well known to those skilled in the art, and poly(amino acids), for example, polypeptides and proteins, peptides, polysaccharides, and combinations thereof. The polyepitopic analytes, to which the subject invention can be applied, can have a large range of molecular weights. For example, in the poly(amino acid) category, the poly(amino acids) of interest will generally be from about 5,000 D to about 5,000,000 D or more molecular weight, and more usually from about 20,000 D to about 1,000,000 D molecular weight. Polyepitopic analytes also can exhibit molecular weights smaller than about 5,000 as well as larger than about 5,000,000 D.

An analyte can be a molecule found directly in a sample such as biological tissue, including body fluids, from a host. Biological tissue includes, for example, excised tissue from an organ or other body part of a host and body fluids, for example, urine, blood, plasma, serum, saliva, semen, stool, sputum, cerebral spinal fluid, tears, mucus, and the like. In addition, a sample can be derived from the environment, for example, air, water, dirt, or from biological materials which are synthetically produced such as libraries of nucleic acids or organic molecules. The sample can be examined directly or can be pretreated to render the analyte more readily detectable. Protein analytes can be released from cells, for example, by lysing the cells and can be isolated using precipitation, extraction, and chromatography. Furthermore, an analyte of interest can be determined by detecting an agent probative of the analyte of interest such as a specific binding pair member complementary to the analyte of interest, whose presence will be detected only when the analyte of interest is present in a sample. Therefore, in such indirect measurements, an agent probative of an analyte becomes the analyte that is detected in an assay.

As used herein, the term "cleavage-inducing moiety" is intended to mean an agent that acts upon a cleavable linkage, or any agent that can produce an agent that acts upon a cleavable linkage, and severs a bond of the cleavage linkage. The cleavage-inducing moiety can be, for example, an enzyme such as a nuclease or protease that can server a phosphodiester or amide bond, respectively. In addition, for example, a cleavage-inducing agent can be an agent that produces singlet oxygen wherein the singlet oxygen is capable of cleaving a suspectible bond within the linkage group. A cleavage-inducing moiety can be added in bulk to a solution that contains a tagged probe with a cleavable linker or a cleavage-inducing moiety be attached or in close proximity to the cleavage-inducing moiety. For example, a cleavage-inducing moiety can be an agent that acts upon a cleavable linkage in a second reagent and thereby potentiates the release of a portion of the second reagent and the released portion is detected.

The nature of the cleavage-inducing moiety that is, or produces, an agent that acts upon a cleavable linkage is dependent on the nature of the cleavable linkage so that they are compatible pairs. For example, a nuclease as a cleavage-inducing moiety and a nuclease-sensitive bond, such as a phosphodiester bond in a nucleic acid sequence, are compatible pairs since the nuclease can cleavage the nuclease-sensitive bond. In addition, a cleavage-inducing moiety can produce an agent and that agent is paired with a bond that is cleavable by the agent. For example, a sensitizer can produce singlet oxygen and then singlet oxygen can cleave a thioether bond.

A cleavage-inducing moiety or agent can be an active species such as, for example, a chemical species that exhibits relatively short-lived activity. Illustrative species include singlet oxygen, hydrogen peroxide, NADH, and hydroxyl radicals, phenoxyradical, superoxide, and the like. Singlet oxygen can be generated from oxygen by dye-sensitized photoexcitation. Singlet oxygen can also be produced by non-photochemical means. One means is by the reaction between hydrogen peroxide and sodium hypochlorite or sodium molybdate, as shown below:

$$H_2O_2 + NaOCl \rightarrow {}^1O_2 + H_2O + NaCl$$

Another means is by reaction between ozone and triphenyl phosphite:

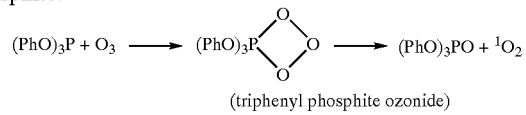

(triphenyl phosphite ozonide)

A third means is by the reaction between triethylsilane and ozone:

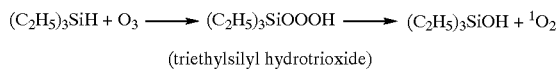
(triethylsilyl hydrotrioxide)

The cleavage-inducing moiety can be a compound that upon activation produces energy as the active agent where energy transfer results in the cleavage of the cleavable linkage. For example, with a Norrish type 2 reaction of onitrobenzyl ethers, or anthracene derivatives, upon excitation with light, the energy is dissipated by cleavage of a bond, rather than emission of light or heat.

For the cognate cleavable linkage, there are a large number of different functional entities that are stable under the conditions used for binding events with a binding compound that can then be cleaved without adversely affecting the tag reporter. Functional entities can be cleaved by chemical or physical methods, involving oxidation, reduction, solvolysis, for example, hydrolysis, photolysis, thermolysis, electrolysis, and chemical substitution. Specific functional entities include, for example, thioethers that can be cleaved with singlet oxygen, disulfide that can be cleaved with a thiol, diketones that can be cleaved by permanganate or osmium tetroxide, β-sulfones, tetralkylammonium, trialkylsulfonium, tetralkylphosphonium, where the α-carbon is activated with carbonyl or nitro, that can be cleaved with base, quinones where elimination occurs with reduction, substituted benzyl ethers that can be cleaved photolytically, carbonates that can be cleaved thermally, metal chelates, where the ligands can be displaced with a higher affinity ligand, as well as many other functional entities that are known in the literature. Cleavage methods are described, for example, in U.S. Pat. Nos. 5,789,172 and 6,001,579 and references cited therein. Other labile groups can be used as alternatives to moieties cleavable by reaction with singlet oxygen such as those disclosed in, for example, Brown, *Contemporary Organic Synthesis* 4(3):216–237 (1997), and as will be apparent to one skilled in the art.

Association of a cleavage-inducing moiety with an analyte can be accomplished in a variety of ways, for example, the cleavage-inducing moiety can be associated with the analyte through a target-binding moiety. A cleavage-inducing moiety linked to a target-binding moiety is called a "cleavage-inducing reagent" and is described further below. However, the cleavage-inducing moiety also can be associated with an analyte in the absence of a target-binding moiety in the cleavage-inducing reagent. For example, the cleavage-inducing moiety can be associated directly with the analyte either by attachment, incorporation, absorption, dissolution, surface adsorption, and the like. In one example, a cleavage-inducing moiety can be incorporated into a cell membrane, for example, to study cellular proteins and their interactions or intercalated into a polynucleotide duplex.

One particular embodiment of a cleavage-inducing moiety includes a "sensitizer" which is a class of chemical moiety that can produce a short-lived active species such as, for example, singlet oxygen. Therefore, a sensitizer is a molecular class of compounds or reactants that can generate reactive intermediates. Generally, a sensitizer is a photosensitizer. However, other sensitizers can be employed in the present invention including, for example, chemi-activated sensitizer, such as enzymes and metal salts and other substances and compositions that can produce reactive intermidiates with or without activation by an external light source. Specific examples of such other subtances include, molybdate ($MoO_4^=$) salts and chloroperoxidase and myeloperoxidase plus bromide or chloride ion (Kanofsky, *J. Biol. Chem.* 259:5596 (1983)) which catalyze the conversion of hydrogen peroxide to singlet oxygen and water. For the above examples of sensitizers, hydrogen peroxide can be included as an ancillary reagent, chloroperoxidase can be bound to a surface and molybdate can be incorporated in the aqueous phase of a liposome, respectively. Other sensitizers included within the scope of the invention are compounds that are not true sensitizers but which on excitation by heat, light, ionizing radiation, or chemical activation will release a molecule of singlet oxygen. The members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

Photosensitizers are sensitizers for generation of singlet oxygen by excitation with light or other source of irridiation and include, for example, dyes and aromatic compounds. General characteristics of such compounds include, for example, covalently bonded atoms, usually with multiple conjugated double or triple bonds. The compounds generally absorb light in the wavelength range of about 200 to about 1,100 nm, usually, about 300 to about 1,000 nm, preferably, about 450 to about 950 nm, with an extinction coefficient at its absorbance maximum greater than about 500 $M^{-1}$ $cm^{-1}$, preferably, about 5,000 M−1 cm−1, more preferably, about 50,000 $M^{-1}$ $cm^{-1}$, at the excitation wavelength. The lifetime of an excited state produced following absorption of light in the absence of oxygen will usually be at least about 100 nanoseconds, preferably, at least about 1 millisecond. In general, the lifetime is sufficiently long to permit cleavage of a linkage in a reagent in accordance with the present invention. The photosensitizer excited state usually has a different spin quantum number (S) than its ground state and is usually a triplet (S=1) when the ground state, as is usually the case, is a singlet (S=0). Generally, the photosensitizer has a high intersystem crossing yield. That is, photoexcitation of a photosensitizer usually produces a triplet state with an efficiency of at least about 10%, desirably at least about 40%, generally greater than about 80%.

Photosensitizers chosen are relatively photostable and, generally, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they can have extended aromatic structures.

Photosensitizers can include, for example, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment, for example, to a target-binding moiety. Examples of other photosensitizers that can be utilized in the present invention are those that have the above properties and which can be found enumerated in, for example, N. F. Turro, "Molecular Photochemistry" page 132, W. A. Benjamin Inc., N.Y. 1965. Other sensitizers for generation of singlet oxygen are discussed in, for example, Ullman, et al., Proc. Natl. Acad. Sci. USA 91, 5426–5430 (1994). Examples of combinations that find use in this invention can be found in U.S. Pat. Nos. 5,536,498; 5,536,834; and references cited therein; H. H. Wasserman and R. W. Murray. Singlet Oxygen. Academic Press, New York (1979); A. L. Baumstark, Singlet Oxygen, Vol. 2, CRC Press Inc., Boca Raton, Fla. 1983.

A sensitizer reagent generally contains a sensitizer and, where the sensitizer is not otherwise able to be associated with the analyte, a binding partner for the analyte, which is usually a member of a specific binding pair, or an analyte analog. The binding partner usually has a high affinity for the analyte. Usually, the binding affinity will be at least about $10^{-7}M^{-1}$, more usually, at least about $10^{-8}M^{-1}$. In one embodiment, the binding partners are receptors, which include antibodies, IgA, IgD, IgG, IgE and IgM and subtypes thereof, enzymes, lectins, nucleic acids, nucleic acid binding proteins, or any other molecule that provides the desired specificity for the analyte in the assay. The antibodies can be polyclonal or monoclonal or mixtures of monoclonal antibodies depending on the nature of the target composition and the targets.

A "cleavage-inducing reagent" generally consists of two components, a target-binding moiety and a cleavage-inducing moiety. The target-binding moiety for the cleavage-inducing reagent is chosen such that positioning of the cleavage-inducing reagent in close proximity to a tagged probe is dependent on the presence of analyte. The target-binding moiety can be, for example, a binding partner for the analyte that directly binds to the analyte, or alternatively, an analyte analog that binds to a binding partner for the analyte. The nature of the target-binding moiety in the cleavage-inducing reagent depends on the nature of the assay to be conducted, for example, competitive or sandwich, and so forth.

Attachment of a target-binding moiety to the cleavage-inducing moiety can be direct or indirect, covalent or non-covalent and can be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970). A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds is well known and is amply illustrated in the literature (see above). The length of a linking group to a target-binding moiety can vary widely, depending upon the nature of the compound being linked, the effect of the distance on the specific binding properties and the like.

The cleavage-inducing reagent can be pre-formed or formed in situ. In the former circumstance the cleavage-inducing reagent has all of its components bound together prior to use in the present methods. In the latter situation at least some of the components of the cleavage-inducing reagent are added separately to a medium in which the present methods are conducted. In one approach the binding partner for the analyte, which is one component of the cleavage-inducing reagent, is added to the medium to bind to analyte if present in the medium. The binding partner comprises a moiety for attachment of the cleavage-inducing moiety of the cleavage-inducing reagent. Usually, this involves a second moiety, which is present on the cleavage-inducing moiety, where the second moiety and the moiety of the binding partner interact providing for attachment of the sensitizer to the binding partner and formation of the cleavage-inducing reagent in situ. Typically, the moieties interact by non-covalent attachment. This situation is exemplified by one of the two moieties comprising a small molecule and the other of the moieties comprising a binding partner for the small molecule. For example, the small molecule can be biotin, digoxin, fluorescein, dinitrophenol, and so forth, and the binding partner for the small molecule is, respectively, avidin, antibody for digoxin, antibody for fluorescein, antibody for dinitrophenol, and so forth.

It can be desirable to have multiple cleavage-inducing moieties attached to a target-binding moiety to increase, for example, the number of active species generated. Where the target-binding moiety has a plurality of sites for attachment such as, for example, a poly(amino acid), such as an antibody, there are a plurality of binding sites on the poly(amino acid) for attachment of cleavage-inducing moieties. To further enhance the number of cleavage-inducing moieties, a hub molecule or nucleus can be employed. The hub nucleus is a polyfunctional material, normally polymeric, having a plurality of functional groups, e.g., hydroxy, amino, mercapto, carboxy, ethylenic, aldehyde, etc., as sites for linking. The functionalities on the hub should be those that are reactive with a functionality on the cleavage-inducing moiety or the target-binding moiety to be attached.

In certain embodiments the cleavage-inducing reagent comprises a support with which one of the components of the cleavage-inducing reagent is associated. The support can be comprised of an organic or inorganic, solid or fluid, water insoluble material, which can be transparent or partially transparent. The support can have any of a number of shapes, such as particle including bead, film, membrane, tube, well, strip, rod, and the like. For supports in which a sensitizer is incorporated, the surface of the support is, preferably, hydrophilic or capable of being rendered hydrophilic and the body of the support is, preferably, hydrophobic. The support can be suspendable in the medium in which it is employed. Examples of suspendable supports, by way of illustration and not limitation, are polymeric materials such as latex, lipid bilayers, oil droplets, cells and hydrogels. Other support compositions include glass, metals, and polymers, either used by themselves or in conjunction with other materials. Binding of target binding moieties to the support can be direct or indirect, covalent or non-covalent and can be accomplished by well-known techniques, commonly available in the literature as discussed above. See, for example, "Immobilized Enzymes," Ichiro Chibata, supra. The surface of the matrix can be polyfunctional or be capable of being polyfunctionalized or be capable of binding to a target-binding moiety, or the like, through covalent or specific or non-specific non-covalent interactions.

The invention provides methods for identifying a target analyte. The methods of the invention are advantageous for detecting multiple analytes simultaneously in a single sample. Large sets of tagged probes can be generated that allow for the simultaneous detection of multiple analytes. As described further above, a tagged probe generally has a mobility or mass modifying moiety, a target-binding moiety, and a cleavable linking group that links the mobility or mass modifier to the target-binding moiety. After binding to a target analyte, a unique tag reporter is cleaved from the tagged probe and the tag reporter identifies the tagged probe it originates from.

Each released tag reporter has a unique physical characteristic that allows it to be uniquely identified when compared to other tag reporters used in the same assay. The tag reporters can be separated and identified based on this difference. For example, tag reporters can differ from each other based on a unique mass or a unique charge or a unique mass-to-charge ratio. Methods for separating and identifying tag reporters based on these physical differences include, for example, electrophoresis, chromatography, and mass spectrometry.

Electrophoresis is a convenient technique for separating tag reporters. Each tag reporter will have a different mobility through the gel based on its unique mass and charge characteristics. Although not required, a tag reporter detected by electrophoresis can have a detection group or moiety, such as a fluorophore, attached to aid in detection. Fluorescently labeled tag reporters can be separated and identified, for example, using the same gel electrophoresis and detection system used for automated sequencing.

Mass spectrometry can also be used to separate and identify tag reporters. Tag reporters can be ionized in a mass spectrometer and the ions separated in space or time based on their mass-to-charge ratio. The mass spectrometer then calculates a mass associated with each ion. Therefore, when referring to mass spectrometry, the term mass can be used for simplicity to describe a mass-to-charge ratio.

Mass spectrometry is a sensitive and accurate technique for separating and identifying molecules. Generally, mass spectrometers have two main components, an ion source for the production of ions and a mass-selective analyzer for measuring the mass-to-charge ratio of ions, which is and converted into a measurement of mass for these ions. Several ionization methods are known in the art and described herein. A tag reporter can be charged prior to, during or after cleavage from the tagged probe. Consequently, a tagged reporter that will be measured by mass spectrometry does not require a charge since a charge can be acquired through the mass spectrometry procedure. In mass spectrometry analysis, optional components of a tagged probe such as charge and detection moieties can be used to contribute mass to the tag reporter.

Different mass spectrometry methods, for example, quadrupole mass spectrometry, ion trap mass spectrometry, time-of-flight mass spectrometry and tandem mass spectrometry, as described herein, can utilize various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions. The ability to precisely control the movement of ions in a mass spectrometer allows for greater options in detection protocols which can be advantageous when a large number of tag reporters, for example, from a multiplex experiment, are being analyzed. For example, in a multiplex experiment with a large number of tag reporters it can be advantageous to select individual reporters from a group of similar reporters and then analyze that reporter separately. Another advantage based on controlling the mass range detected by the mass spectrometer includes the ability to exclude un-cleaved or partially-cleaved tagged probes from being analyzed which reduces background noise from the assay.

Mass spectrometers can resolve ions with small mass differences and measure the mass of ions with a high degree of accuracy. Therefore, tag reporters of similar masses can be used together in the same experiment since the mass spectrometer can differentiate the mass of even closely related tags. The high degree of resolution and mass accuracy achieved using mass spectrometry methods allows the use of large sets of tagged probes because the resulting reporter tags can be distinguished from each other. The ability to use large sets of tagged probes is an advantage when designing multiplex experiments.

Another advantage of using mass spectrometry for detecting the mass of a tag reporter is based on the high sensitivity of this type of mass analysis. Mass spectrometers achieve high sensitivity by utilizing a large portion of the ions that are formed by the ion source and efficiently transmitting these ions through the mass analyzer to the detector. Because of this high level of sensitivity, even limited amounts of sample can be measured using mass spectrometry. This can be an advantage in a multiplex experiment where the amount of each tag reporter species may be small.

Mass spectrometry methods are well known in the art (see Burlingame et al. Anal. Chem. 70:647R–716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass.

The movement of gas-phase ions can be precisely controlled using electromagnetic fields generated in the mass spectrometer. The movement of ions in these electromagnetic fields is proportional to the m/z of the ion and this forms the basis of measuring the m/z and therefore the mass of a sample. The movement of ions in these electromagnetic fields allows the ions to be contained and focused which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass anlayzer generally define the type of instrument and its capabilities. For example, an inlet can be a capillary-column liquid chromatography source or can be a direct probe or stage such as used in matrix-assisted laser desorption. Common ion sources are, for example, electrospray, including nano-spray and microspray or matrix-assisted laser desorption. Exemplary mass analyzers include a quadrupole mass filter, ion trap mass analyzer and time-of-flight mass analyzer.

The ion formation process is a starting point for mass spectrum analysis. Several ionization methods are available and the choice of ionization method depends on the sample to be analyzed. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix. Other ionization procedures known in the art include, for example, plasma and glow discharge, plasma desorption ionization, resonance ionization, and secondary ionization. A tag reporter can become ionized prior to, during, or after cleavage from the tagged probe.

Electrospray ionization (ESI) has several properties that are useful for the invention described herein. For example, ESI can be used for biological molecules such as polypeptides that are difficult to ionize or vaporize. In addition, the efficiency of ESI can be very high which provides the basis for highly sensitive measurements. Furthermore, ESI produces charged molecules from solution, which is convenient for anlayzing tag reporters that are in solution. In contrast, ionization procedures such as MALDI require crystallization of the sample prior to ionization.

Since ESI can produce charged molecules directly from solution, it is compatible with samples from liquid chromatography systems. For example, a mass spectrometer can have an inlet for a liquid chromatography system, such as an HPLC, so that fractions flow from the chromatography column into the mass spectrometer. This in-line arrangement of a liquid chromatography system and mass spectrometer is sometimes refered to as LC-MS. A LC-MS system can be used, for example, to separate un-cleaved or partially cleaved tag reporters from cleaved tag reporters before mass spectrometry analysis. In addition, chromatography can be used to remove salts or other buffer components from the tag reporter sample before mass spectrometry analysis. For example, desalting of a sample using a reversed-phase HPLC column, in-line or off-line, can be used to increase the efficiency of the ionization process and thus improve sensitivity of detection by mass spectrometry.

A variety of mass analyzers are available that can be paired with different ion sources. Different mass analyzers have different advantages as known to one skilled in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering. This will be of use in tandem mass spectrometry as described further below.

A quadrupole mass analyzer, as well as the other mass analyzers described herein, can be programmed to analyze a defined m/z or mass range. This property of mass spectrometers is useful for the invention described herein. Since the mass range of cleaved tag reporters will be known prior to an assay, a mass spectrometer can be programmed to transmit ions of the projected correct mass range while excluding ions of a higher or lower mass range. The ability to select a mass range can decrease the background noise in the assay and thus increase the signal-to-noise ratio. In addition, a defined mass range can be used to exclude analysis of any un-cleaved or partially-cleaved tagged probes, which would be of higher mass than the mass of the fully-cleaved tagged probes (tag reporters). Therfore, the mass spectrometer can accomplish an inherent separation step as well as detection and identification of the tag reporters.

Ion trap mass spectrometry utilizes an ion trap mass analyzer. In these mass analyzers, fields are applied so that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadrupole mass filters, although ion traps do have low m/z limitations.

Time-of-flight mass spectrometry utilizes a time-of-flight mass analyzer. For this method of m/z analysis, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

One consideration in this type of mass analysis is that the set of ions being studied be introduced into the analyzer at the same time. For example, this type of mass analysis is well suited to ionization techniques like MALDI which produces ions in short well-defined pulses. Another consideration is to control velocity spread produced by ions that have variations in their amounts of kinetic energy. The use of longer flight tubes, ion reflectors, or higher accelerating voltages can help minimize the effects of velocity spread. Time-of-flight mass analyzers have a high level of sensitivity and a wider m/z range than quadrupole or ion trap mass analyzers. Also data can be acquired quickly with this type of mass analyzer because no scanning of the mass analyzer is necessary.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisinally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans. The use of these different tandem mass spectrometry scan procedures can be advantageous when large sets of reporter tags are measured in a single experiment as with multiplex experiments.

The invention provides methods for detecting a variety of target analytes including nucleic acids, and polypeptides such as specific binding pairs of polypeptides. Several different combinations of cleavable linkages and cleavage-inducing moieties, for example nucleases or visible light, can be utilized in the invention. In addition, the invention provides methods for detecting a variety of target analytes using tagged probes with various configurations. For example, a tagged probe can contain a cleavage-inducing moiety directly attached to the tagged probe. In addition, for example, a cleavage-inducing moiety and cleavable tag reporter can be on separate reagents that are brought into proximity to each other resulting in release of a tag reporter.

The invention provides a method for detecting a target nucleic acid sequence by: (a) contacting one or more target nucleic acid sequences with a set of tagged probes under conditions sufficient for hybridization of a target nucleic acid sequence with a tagged probe, where the tagged probes contain a mass modifier region attached to a nucleic acid target binding moiety by a bond that is cleavable by a nuclease, and where the nucleic acid target binding moiety contains at least one bond that is resistant to the nuclease; (b) treating the tagged probe hybridized to the target nucleic acid with a nuclease under conditions sufficient for cleavage of the nuclease-cleavable bond to release a tag reporter, and (c) detecting a mass of the tag reporter, where the mass uniquely corresponds to a known target sequence. The mass of a tag reporter in the method can be determined, for example, using a mass spectrometry method such as quadrupole mass spectrometry, ion trap mass spectrometry, time-of-flight mass spectrometry or tandem mass spectrometry.

The method can further include an additional step of separating one or more cleaved tagged probes from un-cleaved or partially-cleaved tagged probes. Separation can be accomplished using capture ligands, such as biotin or other affinity ligands, and capture agents, such as avidin, streptavidin, an antibody, a receptor, or a functional fragment thereof, having specific binding activity to the capture ligand. A tagged probe, or a target-binding moiety of a tagged probe, can contain a capture ligand having specific binding activity for a capture agent. For example, the target-binding moiety of a tagged probe can be biotinylated or attached to an affinity ligand using methods well known in the art. After the tag reporter is cleaved from the tagged probe, the remaining part of the tagged probe with the target-binding moiety and biotin can be removed by, for example, strepavidin agarose beads. A capture ligand and capture agent can also be used to add mass to the remaining part of the tagged probe such that it can be excluded from the mass range of the tag reporters detected in a mass spectrometer.

A separtation step can also be used to remove salts, enzymes, or other buffer components from the tag reporter sample. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniturized apparatus is used, a micro-affinity chromatography separation step can be used. In addition, whether a separation step is desired, and the choice of separation method, can depend on the detection method used. For example, the efficiency of matrix-assisted laser desorption/ionization and electrospray ionization can be improved by removing salts from a sample. For example, salts can absorb energy from the laser in matrix-assisted laser desorption/ionization and result in lower ionization efficiency.

A nuclease can cleave any bonds in the target-binding moiety or target nucleic acid that are nuclease-susceptible. However, an advantage of having at least one nuclease-resistant bond in the target-binding moiety is that a tagged probe will yield a single sized species of released tag reporter upon cleavage. Nuclease-cleavable bonds can include, for example, a phosphodiester bond, and nuclease-resistant bonds can include, for example, thiophosphate, phosphinate, phosphoramidate, or a linker other than a phosphorous acid derivative, such as amide and boronate linkages.

Several nucleases are known in the art that can be used to cleave different types of nucleic acids. For example, nucleases are available that can cleave double-stranded DNA, for example, DNAse I and Exonuclease III, or single-stranded DNA, for example, nuclease S1. Nucleases include enzymes that function solely as nucleases as well as multi-functional enzymes that contain nuclease activity such as, for example, DNA polymerases like Taq polymerase that have 5' nuclease activity. Several derivatives of Taq polymerases derived from different bacterial species or from designed mutations are known which cleave specific structures of nucleic acid hybrids (Kaiser et al., *J. Biol. Chem.* 274:21387–21394 (1999); Lyamichev et al., *Proc. Natl. Acad. Sci. USA* 96:6143–6148 (1999); Ma et al., *J. Biol. Chem.* 275:24693–24700 (2000)). For example, Cleavase™ enzymes (Third Wave Technologies) have been developed that cleave only at specific nucleic acid structures.

A target nucleic acid used in the methods of the invention can include any nucleic acid that can be bound by a tagged probe. For example, RNA or single-stranded or double-strand DNA. In one embodiment, the target nucleic acid can be a single nucleotide polymorphism (SNP).

For detecting SNPs, various techniques can be employed of varying complexity. In one embodiment, a primer can be employed that terminates at the nucleotide immediately preceding the SNP. The tag reporter can be bound to the primer and a ligand can be bound to the nucleotide reciprocal to the SNP. In one approach, four vessels can be used, each with a different labeled nucleotide, for example, each nucleotide can have, or be made to have, different masses in a mass spectrometer. In another approach, one vessel can be employed with each of the labeled nucleotides having a different mass modifier. The primers can be extended and then captured, for example, by having an affinity ligand, such as biotin attached to the nucleotide, and contacting the extension mixture with the reciprocal receptor, such as streptavidin, bound to a support. The tag reporter can then released by, for example, a nuclease and analyzed. By grouping targets of interest having the same nucleotide for a SNP, the assay can be multiplexed for a plurality of targets. Other methods include having probes where the SNP is mismatched. The mismatching nucleotide is labeled with the tag reporter. When the SNP is present, the tag reporter labeled nucleotide will be released for detection, for example, by mass spectrometry. See U.S. Pat. No. 5,811, 239.

Each SNP detection sequence can have at least one nucleotide modified with a tagged probe, which can be detected, for example, by mass spectrometry. Usually, the modified nucleotide will be at the 5' end of the sequence, but the modified nucleotide can be anywhere in the sequence, particularly where there is a single nuclease susceptible linkage in the detection sequence. Since the determination is based on at least partial degradation of the SNP detector sequence, having the modified nucleotide at the end ensures that if degradation occurs, the tag reporter will be released. Since nucleases can cleave at other than the terminal phosphate link, it is desirable to prevent cleavage at other than the terminal phosphate link. In this way one avoids the confusion of having the same tag reporter joined to different numbers of nucleotides after cleavage. Therefore, specific signal to noise can be increased using nuclease resistant bonds at positions distal to the cleavable linkage. Cleavage at the terminal phosphate can be relatively assured by using a linker that is not cleaved by the nuclease, more particularly having only the ultimate linkage susceptible to hydrolysis by a nuclease. If desired, all of the linkers other than the ultimate linker can be resistant to nuclease hydrolysis.

A plurality of SNPs or other polymorphisms can be simultaneously determined by combining target DNA with a plurality of reagent pairs under conditions of primer extension. Each pair of reagents includes a primer which binds to target DNA and a SNP detection sequence, normally labeled, which binds to the site of the SNP and has a tag, usually at its 5' end and the base complementary to the SNP, usually at other than a terminus of the SNP detection sequence. The conditions of primer extension can employ a polymerase having 5'–3' exonuclease activity, dNTPs and auxiliary reagents to permit efficient primer extension. The primer extension is performed, whereby detector sequences bound to the target DNA are degraded with release of the tag. By having each SNP associated with its own tag, one can determine the SNPs which are present in the target DNA for which pairs of reagents have been provided. In one SNP determination protocol, the primer includes the complementary base of the SNP. This protocol is referred to as Invader™ technology, and is described in U.S. Pat. No. 6,001,567.

In another embodiment, a plurality of oligonucleotide probes or a target polynucleotide sample can be bound to a surface of a solid support such as an array. Arrays can be convenient for handling a large number of nucleic acid probes when performing multiplex assays. Methods for constructing arrays are well known in the art. See, for example, U.S. Pat. No. 5,744,305 (Fodor, et al.); PCT application WO 89/10977; Gamble, et al., WO97/44134; Gamble, et al., WO98/10858; Baldeschwieler, et al., WO95/25116; Brown, et al., U.S. Pat. No. 5,807,522; and the like.

Another embodiment of the invention utilizes a cleavage-inducing moiety that is physically attached to the tagged probe. For example, a tagged probe can contain a tag reporter region attached to a target-binding moiety by a bond that is cleavable when the attached cleavage-inducing moiety is activated. An advantage to having the cleavage-inducing moiety attached to the tagged probe is that the cleavage agent is produced locally and in a one-to-one correspondence to tag reporter. This arrangement, and other close proximal arrangements as described further below, can facilitate both an increase in specific signal and a decrease in non-specific background or noise. The proximity of the cleavage-inducing moiety to the cleavable linker increases the likelihood of cleavage, thus increasing the signal. A further advantage to having the cleavage-inducing moiety attached or in close proximity to the cleavable linker is that this moiety is less likely to be involved in non-specific cleavage reactions. Therefore, proximal arrangements of the cleavage-inducing moiety to the cleavable linker lead to a better signal-to-noise ratio in the assay.

Another advantage to proximal arrangements of the cleavage-inducing moiety to the cleavable linker can be a reduction in undesirable side reactions if the cleavage agent is, for example, toxic, volatile, or highly reactive. Another way to avoid undesirable side reactions is to use a gentle cleavage agent, for example, visible light. This type of cleavage can be advantageous when assaying biomolecules such as nucleic acids and proteins which can be damaged by reagents such as ultra-violet light, strong acids or bases, but are stable in the presence of visible light.

The invention provides a method for detecting a target analyte by contacting a target analyte with a set of tagged probes attached to a cleavage-inducing moiety under conditions sufficient for binding of the analyte with a tagged probe, where the tagged probes contain a mass modifier region attached to a target binding moiety by a cleavable linkage and where the cleavable linkage is susceptible to cleavage when the cleavage-inducing moiety is activated by visible light; separating tagged probes bound to a target binding moiety from unbound tagged probes; activating the cleavage-inducing moiety with visible light to release a tag reporter; and detecting a mass of the tag reporter, where the mass uniquely corresponds to a known target analyte. As above, the mass of the tag reporter can be detected using a mass spectrometry method such as quadrupole mass spectrometry, ion trap mass spectrometry, time-of-flight mass spectrometry or tandem mass spectrometry. The unbound tagged probes can be separated from the bound probes using several methods. For example, when the analyte is immobilized on a solid support such as a bead or other matrix the unbound tagged probes can be eliminated using a wash step. In addition, for example, if the analyte is in solution the unbound tagged probe can be separated from the bound probe using standard analytical techniques such as chromatography or electrophoresis. After cleavage, the method can further include an additional step to separate one or more cleaved tagged probes from un-cleaved or partially-cleaved tagged probes using capture ligands and capture agents having specific binding activity to the capture ligand.

In addition, the method can be used in a multiplex format when one or more target analytes further comprise a plurality of different target analytes. As described above, target analytes can be polypeptides, proteins, peptides, polysaccharides, nucleic acids, and small molecules. Therefore, the target binding moiety can be a ligand, antiligand, receptor, antibody, biotin, avidin, strepavidin, protein A and polynucleotide, or a functional fragment thereof, that binds to the target analyte.

One of the advantages of the methods of the invention is the ability to perform multiplex assays. In multiplex assays several analytes can be detected simultaneously. In a multiplex format, sets of tagged probes are used such that the resulting tag reporter has a unique characteristic, for example a unique mass, that differentiates the tag reporter from other tag reporters in the same set. A multiplex experiment can be used to detect 2 or more analytes, 10 or more analytes, 100 or more analytes, 1,000 or more analytes, or 10,000 or more analytes in the same assay. The number of tagged probes used in a multiplex assay is equal to or greater than the number of analytes to be detected. For example, when a multiplex experiment is used to detect 100 analytes, 100 or more tagged probes that result in 100 or more tag reporters of unique mass are used. The number of analytes that can be detected in a single assay is limited only by the number of distinct tag reporters that can be detected in a single assay. As described previously, mass spectrometry can resolve small difference in mass allowing the use of a large number of tag reporters in a single assay.

As described previously, tagged reporters can contain a cleavage-inducing moiety. The cleavage-inducing moiety can further comprise a photosensitizer or a chemi-activated sensitizer. For example, the cleavage-inducing moiety can be a sensitizer capable of generating singlet oxygen and the cleavable linkage can be susceptible to cleavage by singlet oxygen. In addition, the cleavage-inducing moiety can be a sensitizer such as a benzophenome, 9-thioxanthone, eosin, 9,10,-dibromoanthraene, methylene blue, metalloporphyrin, chloroperoxidase or myeloperoxidase. Furthermore, the cleavage-inducing moiety can comprise two or more cleavage-inducing moieties.

In one embodiment, the cleavage-inducing moiety acts in such a manner as to produce an active short-lived species that is able to act upon the cleavable linkage and release the releasable portion only when the two reagents are brought into close proximity in relation to the presence of the analyte. A short-lived species is advantageous to limit undesirable side reactions when the species is toxic, volatile, or highly reactive and to limit non-specific reactions thus reducing background noise in the assay. In one embodiment of the present invention the first reagent is a sensitizer reagent capable of generating singlet oxygen and the second reagent comprises a portion releasable by the generated singlet oxygen. Singlet oxygen is a short-lived agent and so has the advantages of a short-lived agent as described above. Under the circumstance of the close proximity of the two reagents in relation to the presence of the analyte, the short-lived species is able to cleave the cleavable linkage.

In another embodiment of the invention, a feature involves bringing into close proximity, in relation to the presence of the target analyte, a first reagent that contains a cleavage-inducing moiety and a second reagent that contains a portion that is releasable by the action of the cleavage-inducing moiety. The reagents are brought into close proximity in relation to the presence of the analyte by virtue of some interaction or binding event involving the analyte. The releasable portion is released upon activation of the cleavage-inducing moiety when the analyte is present in the sample and influences the extent that the above reagents are brought into close proximity. This close proximal relationship is advantageous in that it results in an increase in specific signal and a decrease in non-specific signal thus improving the signal-to-noise ratio, as described previously. In addition, since the cleavage agent is produced locally, if the cleavage agent is toxic or reactive this arrangement can limit the chance of undesirable side reactions.

The invention provides a method for detecting a target analyte by: (a) contacting a target analyte with a set of first and second binding reagents under conditions sufficient for binding of a target analyte with the first and second binding reagents, where each of the first binding reagents contains a cleavage-inducing moiety and a target binding moiety, and each of the second binding reagents contains a tagged probe having a mass modifier region attached to a target binding moiety by a cleavable linkage, and where the cleavable linkage is susceptible to cleavage when in proximity to an activated cleavage-inducing moiety; (b) activating the cleavage-inducing moiety to release a tag reporter; and (c) detecting a mass of the tag reporter where the mass uniquely corresponds to a known target analyte. The mass of the tag reporter can be detected, for example, using a mass spectrometry method such as quadrupole mass spectrometry, ion trap mass spectrometry, time-of-flight mass spectrometry or tandem mass spectrometry. An additional step that can be added to the method described above is to separate the tagged probes from salts or other buffer components, or to separate one or more of the cleaved tagged probes from un-cleaved or partially-cleaved tagged probes using capture ligands and capture agents having specific binding affinity to the capture ligand.

As described above, the methods, compositions and kits of the invention have particular application to methods for determining one or more analytes in a sample suspected of containing the analytes. For example, the one or more target analytes can be a plurality of different target analytes. In addition, the one or more target analytes can contain a binding partner of a specific binding pair.

The first binding reagents comprises a cleavage-inducing moiety. The cleavage-inducing moiety can further comprise a photosensitizer or a chemi-activated sensitizer.

Assays can be performed in a competitive mode or a sandwich mode. In an example of a competitive mode, the target competes with a labeled binding member for the reciprocal member. In this mode, the binding sites of the reciprocal binding member become at least partially filled by the target, reducing the number of available binding sites for the labeled reciprocal binding member. Thus, the number of labeled binding members that bind to the reciprocal binding member will be in direct proportion to the number of target molecules present. In a sandwich mode, the target is able to bind at the same time to different binding members, that is, a first member and a second member that binds at a site of the target molecule different from the site at which the first member binds. The resulting complex has three components, where the target serves to link the first and second members.

The methodologies that can be employed can be competitive or non-competitive, heterogeneous or homogeneous. Heterogeneous techniques normally involve a separation step, where unbound label is separated from bound label. On the other hand, homogeneous assays do not require, but can employ, a separation step. Non-competitive assays are usually sandwich assays involving the binding of an analyte to two target binding moieties specific for the analyte whereas competitive assays usually involve competition for binding sites between an analyte and an analyte analog.

In addition, in many heterogeneous assays it can be required that the unbound labeled reagent be separable from the bound labeled reagent. This can be achieved in a variety of ways, each requiring a reagent bound to a solid support that distinguishes between the complex of labeled reagent and target. The solid support can have the complex directly or indirectly bound to the support for directly bound, one can have the binding member or tagged probe covalently or non-covalently bound to the support. The solid support can be a vessel wall, for example, microtiter well plate well, capillary, plate, slide, beads, including magnetic beads, liposomes, or the like. The primary characteristics of the solid support is that it permits segregation of the bound labeled specific binding member from unbound probe and that the support does not interfere with the formation of the binding complex, nor the other operations of the determination.

One example of an assay is a sandwich-type immunoassay, which allows for the qualification and quantification of known antigens. In this assay, a matched pair of antibodies forms a sandwich with an antigen bringing the two antibodies in close proximity. One of these antibodies can be conjugated with one or more tag moieties to form a tagged probe. The tag moiety can be linked to an antibody by a singlet oxygen labile linkage, which allows the release of a tag reporter after reaction with singlet oxygen. The second antibody can be conjugated, for example, to a sensitizer dye that produces singlet oxygen when irradiated. When the two antibodies form a sandwich, the singlet oxygen cleaves the cleavable linkage to release a tag reporter. The tag reporter is separately detectable by virtue of, for example, its unique mass. Detection of the reporter is related to the presence of the antigen. In addition, detection of the reporter is related to the amount of the antigen.

Figure 3:
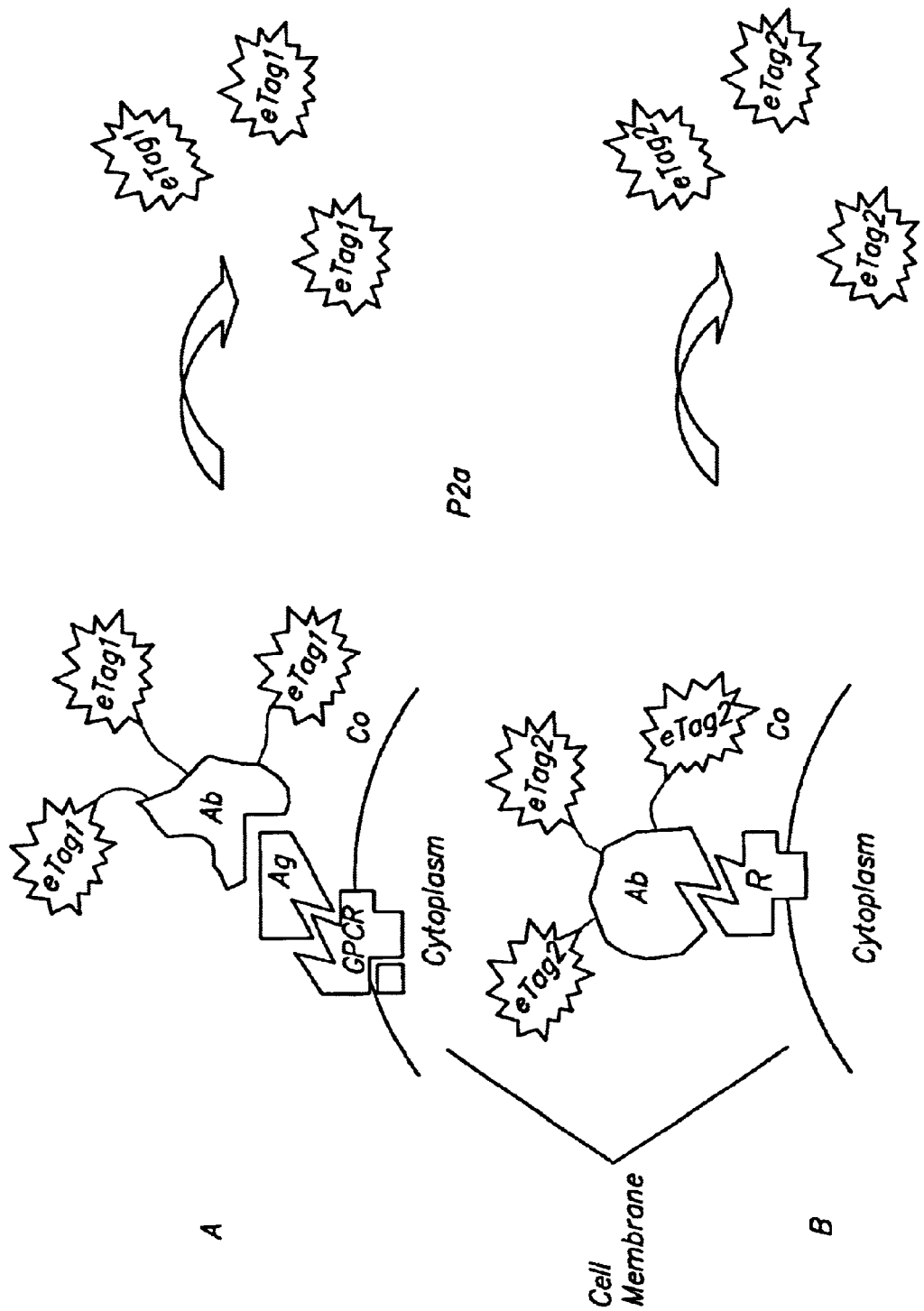
FIGS. 3A and B show schematics depicting multiplexed detection and quantitation of cell surface receptors.

One particular embodiment of a method of use in accordance with the present invention is a multiplexed quantitation of cell surface receptors. Referring to FIG. 3A, a cell membrane is shown exhibiting a GPCR receptor present on the cell membrane. Co represents a cofactor for the binding of a protein antigen to the GPCR receptor. The tagged probe reagent is depicted as an antibody (Ab) with several tag moieties releasably linked thereto. Another reagent is the cleavage-inducing reagent, which can be bound to the surface of the cell membrane by a component that specifically binds to a component of the cell surface that is not the subject of the method, for example, a generic receptor. Alternatively, the cleavage-inducing reagent can be incorporated into the cell membrane, as will described further below. When the receptor is present, the protein antigen binds to it and then the Ab binds to the antigen, bringing the releasable tag moiety in close proximity to the cleavage-inducing reagent. After cleavage, the tag reporters are released, detected and quantitated, and related to the amount of the receptor present. This embodiment can be employed to screen numerous proteins for their ability to interact with the receptor on the cell surface.

A variation of the above is depicted in 3B. The receptor on the cell surface is represented by R. As in FIG. 3A, the tagged probe reagent is depicted as an antibody (Ab) with several tag moieties releasably linked thereto. Another reagent is the releasing inducing reagent as discussed above. When the receptor is present, Ab binds to the receptor bringing the releasable tag moiety in close proximity to the release-inducing reagent. The tag reporters are released, detected and quantitated and related to the amount of the receptor present. This embodiment can be employed to screen numerous cell lysates for the presence of the receptor of interest. Numerous antibody reagents can be employed to screen a cell lysate for the presence of proteins of interest in a single assay.

In addition to identifying a target analyte or analytes, this embodiment also can be used to determine whether two target-binding moieties are able to bind to the same analyte. For example, this method can be used to determine whether two target-binding moieties, such as two antibodies, are able to bind to the same analyte or antigen. The production of a tag reporter would indicate that the two reagents were able to bind the same target thus bringing the reagent with the cleavage-inducing moiety and the reagent with the cleavable linkage into close proximity.

The methods of the invention offer a high degree of versatility for screening unknown materials. The unknown entity can be the target-binding moiety of the tagged probe or of the cleavage-inducing reagent. On the other hand, the unknown entity can be the analyte that can be bound by the target-binding moiety of the tagged probe or the cleavage-inducing reagent or both. Thus, as can be seen, known and unknown entities can be selectively chosen for the reagents and the analyte by the skilled artisan to accommodate a broad range of potential assays and needs.

The methods described previously for detecting a target nucleic acid also can be performed using a cleavage-inducing moiety other than a nuclease. For example, the determination of a target nucleic acid can be performed using two oligonucleotide probes, each binding to different regions of the target polynucleotide. One of the oligonucleotide probes can be labeled with a cleavage-inducing moiety such as a sensitizer and the other oligonucleotide probe can be a tagged probe. The oligonucleotide probes can be selected so that they bind to regions of the target nucleic acid that permit the cleavage-inducing moiety and the cleavable linkage to be brought into proximity when the target nucleic acid is hybridized. Upon binding of all three components and activation of the cleavage-inducing moiety, the cleavable linkage is cleaved releasing the tag reporter of the tagged probe.

The cleavage-inducing moiety and the tag moiety can be linked to their respective oligonucleotide probes at the 3'-end or the 5'-end or at any point that is feasible along the nucleotide chain. One consideration is that the cleavage-inducing moiety and the cleavable linkage be brought into sufficient proximity upon hybridization to the target nucleic acid that the cleavable linkage can be cleaved. In one approach the 3'-end of one oligonucleotide probe is labeled with either the cleavage-inducing moiety or a tag moiety and the 5'-end of the other oligonucleotide probe is labeled with the other of the above moieties. In this approach the oligonucleotide probes are designed so that the binding to the target nucleic acid brings the labeled ends internal to the duplexes formed. In other words the 3'-end labeled oligonucleotide probe binds downstream on the target sequence from the region to which the 5-'end labeled oligonucleotide probe binds.

Another embodiment for detection of a target nucleic acid employs three oligonucleotide probes, each binding to different regions of the target polynucleotide. A first oligonucleotide probe is labeled with an activator moiety that is capable of generating a reaction product, which in turn is able to activate a cleavage-inducing moiety, such as a sensitizer, incorporated in a second oligonucleotide probe. The cleavage-inducing moiety, once activated, is then capable of acting on the third oligonucleotide probe containing a cleavably-linked tag moiety, causing release of a tag reporter. As with the two oligonucleotide approach described above, the three oligonucleotide probes should bind to the target sequence in a manner that brings the activator moiety, cleavage-inducing moiety, and tag moiety into sufficient proximity that the cleavable linkage can be cleaved upon activation. One specific embodiment of this approach would have the three oligonucleotide probes bound adjacently to one another on the target sequence to be detected.

The aforementioned methods can be employed to detect multiple target polynucleotides simultaneously by utilizing appropriate sets of oligonucleotide probes and appropriate tag moieties that permit separation and detection of the released reporter groups, with concomitant identification of the respective target nucleic acids. The methods of the invention are particularly suited for analysis of complex mixtures of target nucleic acids employing array technology and microfluidics.

In a particular embodiment of the above method, the cleavage-inducing moiety is able to intercalate into the nucleic acid duplex created when the oligonucleotide probe binds to a respective target polynucleotide. In this regard the cleavage-inducing moiety can be attached to one of the oligonucleotide probes or it can be a separate reagent. In the latter embodiment a single oligonucleotide probe comprising a tagged moiety can be used for each target nucleic acid. The methods for detecting a target nucleic acid sequence using an oligonucleotide probe containing a cleavage-inducing moiety and an oligonucleotide containing a cleavably-linked tag moiety can also be used to detect a target analyte such as a polypeptide.

The invention also provides a method for identifying a binding partner of a specific binding pair by: (a) incorporating a cleavage-inducing moiety into a first binding partner of a specific binding pair; (b) contacting the first binding partner having an incorporated cleavage-inducing moiety with a set of second binding partners under conditions sufficient for binding, where each of the second binding partners contains a tagged probe having a mass modifier region attached to a target binding moiety by a cleavable linkage, where the cleavable linkage is susceptible to cleavage when in proximity to an activated cleavage-inducing moiety; (c) activating the cleavage-inducing moiety to release a tag reporter, and (d) detecting a mass of the tag reporter, where the mass uniquely corresponds to a known second binding partner of a specific binding pair. The additional step of separating one or more of the cleaved tagged probes from un-cleaved or partially cleaved tagged probes using capture ligands and agents can also be performed as described above. The mass of the tag reporter can be detected, for example, using a mass spectrometry method such as quadrupole mass spectrometry, ion trap mass spectrometry, time-of-flight mass spectrometry or tandem mass spectrometry.

Although the invention has been described above with reference to binding reagents, any of the previously described formats or modes can also be performed by directly incorporating the tagged probe, the cleavage-inducing moiety or both into binding pairs. For example, with protein binding pairs, one protein of a binding pair can be bound by a first reagent that contains a cleavage-inducing moiety and the second protein of a binding pair can be bound by a second reagent that contains a portion that is releasable by the action of the cleavage-inducing moiety. If the two proteins interact, they will be brought into close proximity and a reporter tag will be cleaved and released. A similar method is provided by the invention to screen for a binding partner of a specific binding pair. In this method a cleavage-inducing moiety is incorporated into a first binding partner of a specific binding pair. The first binding partner with the cleavage-inducing moiety is contacted with a set of potential second binding partners that contain a tagged probe with a releasable portion. If two binding partners interact, a tag reporter is cleaved off and released for detection. The unique physical properties of the tag reporter identify the second binding partner.

A cleavage-inducing moiety can be incorporated into a binding partner using chemistry well known in the art. For example, a cleavage-inducing moiety can be linked to a polypeptide, including an antibody, using, for example, carbodiimide conjugation (Bauminger and Wilchek, Meth. Enzymol. 70:151–159 (1980)). In addition EDC also can be used to prepare active esters such as N-hydroxysuccinimide (NHS) ester. The NHS ester, which binds to amino groups can be used to induce the formation of an amino bond with an amino group of a cleavage-inducing moiety or binding partner. Amino-group containing moieites can be found, for example, on polypeptides, antibodies, avidin, H2N-LC biotin, aminodextran or other amino-group containing molecules. Various other methods of incorporation using specific chemistries are well known in the art and can similarly be employed in the methods of the invention for incorporation of a cleavage-inducing moiety into a binding partner.

Figure 4:
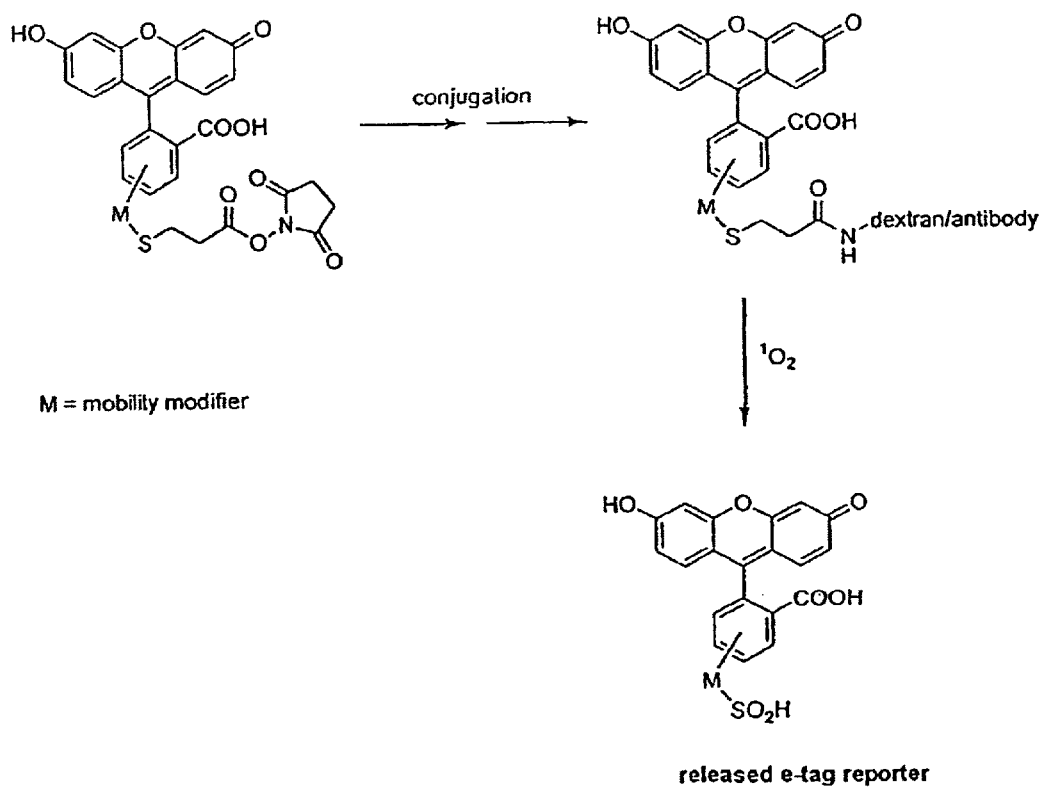
FIG. 4 shows a method for conjugating a tag moiety to an antibody to prepare a tagged probe, and the reaction of the resulting probe with singlet oxygen to produce a sulfonic acid moiety as the realeased tag reporter.

Incorporation of cleavage-inducing moieties or tagged probes into binding pairs can also be used in a multiplex format where the first binding partner contains a plurality of different first binding partners. These different first binding partners can contain distinctive cleavage-inducing moieties. The first binding partner can be, for example, a ligand, antiligand, nucleic acid, or a functional fragment thereof and can contain polypeptides, proteins, peptides, polysaccharides, nucleic acids, and small molecules. In addition, the second binding partner can be a ligand, antiligand, nucleic acid, or a functional fragment thereof. Furthermore, the second binding partner can contain a target binding moiety, for example, a moiety that specifically binds to the first binding partner. This target binding moiety can be a ligand, antiligand, receptor, antibody, biotin, avidin, strepavidin, protein A and polynucleotide, or a functional fragment thereof. FIG. 4 shows a tag moiety can be attached to a second binding partner indirectly, for example, by binding a tagged probe to a molecule, such as an antibody that binds to the second binding partner.

In one embodiment, the methods of the invention can be used to screen for ligands for receptors, for example, to identify ligands for orphan G-protein coupled receptors. There are a large number of specific binding pairs associated with receptors, such as polyclonal and monoclonal antibodies, enzymes, surface membrane receptors, lectins, and ligands for the receptors, which can be naturally occurring or synthetic molecules, protein or non-protein, such as drugs, hormones, and enzymes.

In this embodiment, the first binding partner has an incorporated cleavage-inducing moiety. The cleavage-inducing moiety can further comprise a photosensitizer or a chemi-activated sensitizer. For example, the cleavage-inducing moiety can be a sensitizer capable of generating singlet oxygen and the cleavable linkage can be susceptible to cleavage by singlet oxygen. In addition, the cleavage-inducing moiety can be a sensitizer such as benzophenome, 9-thioxanthone, eosin, 9,10,-dibromoanthraene, methylene blue, metallo-porphyrin, chloroperoxidase or myeloperoxidase. Furthermore, the cleavage-inducing moiety can further comprise two or more cleavage-inducing moieties.

It is understood that modifications which do not substantially affect the activity of the various embodiments of this invention are also included within the definition of the invention provided herein. Accordingly, the following examples are intended to illustrate but not limit the present invention.

EXAMPLE I

Detection of Multiple Tag Reporters Using Mass Spectrometry

Synthesis of Tag Reagents

Conjugation of Sensitizer Molecules to Assay Reagents

Sensitizer molecules can be conjugated to an antibody, antigen, avidin, biotin, mononucleotides, polynucleotides, small molecules, large molecules and others by various methods and configurations. For example, an activated (NHS ester, aldehyde, sulfonyl chloride, etc) sensitizer (Rose Bengal, phthalocyanine, etc.) can be reacted with reactive amino-group containing moieties (antibody, avidin or other proteins, H2N-LC-Biotin, aminodextran, amino-group containing other small and large molecules). The formed conjugates can be used directly (for example the antibody-sensitizer conjugate, Biotin-LC-sensitizer, etc.) in various assays. Also, the formed conjugates can be further coupled with antibody (for example, aminodextran-sensitizer conjugate containing 20–200 sensitizers and 200–500 amino-groups can be coupled to periodate oxidized antibody molecules to generate the antibody-dextran-sensitizer conjugate) or with the antibody and a particle. For example, aminodextran-sensitizer conjugate containing 20–200 sensitizers and 200–500 amino-groups can be coupled to carboxylated polystyrene beads by EDC coupling chemistry to form the sensitizer-aminodextran-particle conjugate. Methods for incorporation of a sensitizer into a particle are given in, e.g., U.S. Pat. No. 5,340,716. Then the Na-periodate oxidized antibody molecules can be reacted with the amino-groups of the aminodextran molecule, in presence of sodium cyanoborohydride, to generate the antibody-dextran-sensitizer-particle conjugate). It should be noted that instead of an antibody molecule, avidin or other molecules can be used.

Preparation of Pro2, Pro4, and Pro6 through Pro13

Pro2, Pro4, Pro6, Pro7, Pro8, Pro9, Pro10, Pro11, Pro12, and Pro13 are carboxyfluorescein-derived tag moieties. The first step involves the reaction of a 5- or 6-FAM with N-hydroxysuccinimide (NHS) and 1,3-dicylcohexylcarbodiimide (DCC) in DMF to give the corresponding ester, which was then treated with a variety of diamines to yield the desired amide, compound 1. Treatment of compound 1 with N-succinimidyl iodoacetate provided the expected iodoacetamide derivative, which was not isolated but was further reacted with 3-mercaptopropionic acid in the presence of triethylamine. Finally, the resulting β-thioacid (compound 2) was converted, as described above, to its NHS ester. The various tag moieties were synthesized starting with 5- or 6-FAM, and one of various diamines (H2N ^ X ^ NH2). The radioisomer of FAM and the chemical entity of "X" within the diamine are indicated in the table below for each of the tag moieties synthesized.

| tag moiety | FAM | X |
| --- | --- | --- |
| Pro2 | 5-FAM | C(CH3)2 |
| Pro4 | 5-FAM | no carbon |
| Pro6 | 5-FAM | (CH2)8 |
| Pro7 | 5-FAM | CH2OCH2CH2OCH2 |
| Pro8 | 5-FAM | CH2CH2OCH2CH2OCH2CH2OCH2CH2 |
| Pro9 | 5-FAM | 1,4-phenyl |
| Pro10 | 6-FAM | C(CH3)2 |
| Pro11 | 6-FAM | no carbon |
| Pro12 | 6-FAM | CH2OCH2CH2OCH2 |
| Pro13 | 6-FAM | CH2CH2OCH2CH2OCH2CH2OCH2CH2 |

Synthesis of Compound 1

To a stirred solution of 5- or 6-carboxyfluorescein (0.5 mmol) in dry DMF (5 mL) were added N-hydroxysuccinimide (1.1 equiv.) and 1,3-dicylcohexylcarbodiimide (1.1 equiv.). After about 10 minutes, a white solid (dicyclohexylurea) started forming. The reaction mixture was stirred under nitrogen at room temperature overnight. TLC (9:1 CH2Cl2-MeOH) indicated complete disappearance of the starting material.

The supernatant from the above mixture was added dropwise to a stirred solution of diamine (2–5 equiv.) in DMF (10 mL). As evident from TLC (40:9:1 CH2Cl2-MeOH—H2O), the reaction was complete instantaneously. The solvent was removed under reduced pressure. Flash chromatography of the resulting residue on Iatrobeads silica provided the desired amine (compound 1) in 58–89% yield. The 1H NMR (300 MHz, DMSO-d6) of compound 1 was in agreement with the assigned structure.

Synthesis of Compound 2

To the amine (compound 1) (0.3 mmol) were sequentially added dry DMF (10 mL) and N-succinimidyl iodoacetate (1.1 equiv.). The resulting mixture was stirred at room temperature until a clear solution was obtained. TLC (40:9:1 CH2Cl2-MeOH—H2O) revealed completion of the reaction. The above reaction solution was then treated with triethylamine (1.2 equiv.) and 3-mercaptopropionic acid (3.2 equiv.). The mixture was stirred at room temperature overnight. Removal of the solvent under reduced pressure followed by flash chromatography afforded the β-thioacid (compound 2) in 62–91% yield. The structure of compound 2 was assigned on the basis of its 1NMR (300 MHz, DMSO-d6).

Synthesis of Pro2, Pro4, and Pro6 through Pro13

To a stirred solution of the β-thioacid (compound 2) (0.05 mmol) in dry DMF (2 mL) were added N-hydroxysuccinimide (1.5 equiv.) and 1,3-dicylcohexylcarbodiimide (1.5 equiv.). The mixture was stirred at room temperature under nitrogen for 24–48 h (until all of the starting material had reacted). The reaction mixture was concentrated under reduced pressure and then purified by flash chromatography to give the target molecule in 41–92% yield.

B. Tag Reporter Assay for Protein Analysis

Direct Conjugation of Tag Moieties to Antibodies

Tag moieties were synthesized with an NHS ester end that reacted with primary amines of the antibody to form a stable amide linkage. This resulted in a random attachment of tag moieties over the surface of the antibody. Modification with up to 6 to 12 NHS ester containing molecules per antibody molecule typically results in no decrease in antigen binding activity. Even higher ratios of NHS ester to antibody are possible with only slight loss of activity.

Protocol

1. Purified human IgG (purchased from Sigma-Aldrich) was diluted to 2 mg/ml in 1× PBS (0.1 M sodium phosphate, 0.15 M NaCl, pH 7.2).
2. NHS ester containing tag moieties was dissolved in DMF (dimethylformamide) to a final concentration between 10 to 20 nmols/μl DMF.
3. 500 μL of diluted human IgG (6.5 nmol) was mixed with either 1, 5, 25, or 50 μl of tag moiety (14, 68, 340, and 680 nmols respectively).
4. The solution was allowed to react for 2 hours on ice in the dark.
5. The tag moiety-conjugated antibody was purified by dialysis against 0.1× PBS (10 mM sodium phosphate, 15 mM NaCl, pH 7.2) for 20 hours at 4° C.

Sandwich Immunoassays for Cytokines

A sandwich-type immunoassay was carried out. The assay allows for the qualification and quantification of known cytokine antigens. In this assay, a matched pair of antibodies forms a sandwich around a cytokine antigen bringing the two antibodies in close proximity. One of these antibodies is conjugated with a tag moiety to yield a tagged probe. The tagged probes have a singlet oxygen labile linkage, which allows the release of the tag reporter after reaction with singlet oxygen. The second antibody is conjugated to a sensitizer dye that produces singlet oxygen when irradiated at 680 nm. Due to the relatively short half-life of the singlet oxygen, only when the two antibodies form a sandwich does the singlet oxygen cleave the cleavable linkage of the tagged probe.

Protocol for a Sandwich Immunoassay for Cytokines 1. 10 μl of assay buffer (0.1× PBS, 40 mg/ml BSA) is mixed with 1 μl (100 nM) of biotin-labeled anti-human IL-4 monoclonal antibody (purchased from Pierce, catalogue number M-450-B) and 1 μl of cytokine IL-4 (Pierce, catalogue number R-IL-4-5) ranging in concentration from 0 to 500 nM.
2. The reaction was allowed to proceed for 30 minutes at room temperature.
3. 5 μl of 100 μg/ml streptavidin-labeled sensitizer beads were added and the mixture was incubated for 15 minutes at room temperature in the dark.
4. To remove non-specific interactions of the tagged probes with streptavidin, 2 μl of 5 μM biotin-DNP was added and incubated for 10 minutes at room temperature in the dark. 1 μl of 400 nM anti-human IL-4 polyclonal antibody conjugated to an amino-dextran tag moiety was added and incubated for 30 minutes at room temperature in the dark.
5. The above procedure was repeated for various cytokines and various tag moieties as follows: IL-6 was studied using tag moiety Pro 10, IFNγ was studied using tag moiety Pro 8, TNFα was studied using tag moiety Pro 7, IL-10 was studied using tag moiety Pro 4, IL-8 was studied using tag moiety Pro 2. A multiplexed assay for six cytokines (IL-4, IL-6, IL-8, IL-10, TNFα, and IFNγ) was conducted.
6. The reaction mixture was then irradiated for 30 s using a 150 watt lamp source with a optical filter of 680 DF+20 nm. The released tag sample is desalted using a reverse phase HPLC column (C18) and analyzed using ESI-TOF mass spectrometry. An electrospray can be produced by application of a high electric field to a small flow of liquid (generally 1–10 μl/min) from a capillary tube. A potential difference of 3–6 kV can be applied between the capillary and counter electrode located 0.2–2 cm away. The high electric field results in formation of highly charged liquid droplets. A mass spectrometer from PerSeptive Biosystems (Farmingham, Mass.) is used to detect the masses of the tag reporters.

All journal article, reference and patent citations provided above, in parentheses or otherwise, whether previously stated or not, are incorporated herein by reference in their entirety.

Although the invention has been described with reference to the disclosed embodiments, those skilled in the art will readily appreciate that the specific experiments detailed are only illustrative of the invention. It should be understood that various modifications can be made without departing from that spirit of the invention.

What is claimed is:

1. A method for detecting one or more target analytes, comprising:
    (a) contacting one or more target analytes with a set of first and second binding reagents under conditions sufficient for binding of a target analyte with said first and second binding reagents, each of said first binding reagents comprising a cleavage-inducing moiety and a target binding moiety, each of said second binding reagents comprising a tagged probe having a mass modifier region attached to a target binding moiety by a cleavable linkage, the mass modifier region of each second binding reagent having a unique mass and said cleavable linkage being susceptible to cleavage when in proximity to said cleavage-inducing moiety;
    (b) activating said cleavage-inducing moieties to cleave the cleavable linkages in proximity thereof so that mass modifier regions are released, and detecting the unique masses of the released mass modifier regions to determine each of the one or more target analytes.

2. The method of claim 1, wherein said mass is detected using a mass spectrometry method selected from the group consisting of quadrupole mass spectrometry, ion trap mass spectrometry, time-of-flight mass spectrometry and tandem mass spectrometry.

3. The method of claim 1, wherein said one or more target analytes further comprise a plurality of different target analytes.

4. The method of claim 1, wherein said one or more target analytes further comprise a binding partner of a specific binding pair.

5. The method of claim 1, wherein said one or more target analytes are selected from a group consisting of polypeptides, proteins, peptides, sugars, polysaccharides, nucleic acids, lipids, and small molecules.

6. The method of claim 1, wherein said first or second binding reagent further comprises a binding partner of a specific binding pair.

7. The method of claim 1, wherein said target binding moiety is selected from the group consisting of ligand, antiligand, receptor, antibody, biotin, avidin, strepavidin, protein A and polynucleotide, or a functional fragment thereof.

8. The method of claim 1, wherein said cleavage-inducing moiety further comprises a photosensitizer or a chemi-activated sensitizer.

9. The method of claim 1, wherein said cleavage-inducing moiety is a sensitizer capable of generating singlet oxygen.

10. The method of claim 8, wherein said cleavage-inducing moiety is a sensitizer selected from the group consisting of benzophenome, 9-thioxanthone, eosin, 9,10,-dibromoanthraene, methylene blue, metallo-porphyrins, chloroperoxidase and myeloperoxidase.

11. The method of claim 1, wherein said cleavage-inducing moiety further comprises two or more cleavage-inducing moieties.

12. The method of claim 1, wherein said mass modifier region further comprises two or more mass modifier regions.

13. The method of claim 1, wherein said cleavable linkage is susceptible to cleavage by singlet oxygen.

14. The method of claim 1, wherein said tagged probes further comprise a capture ligand having specific binding activity for a capture agent.

15. The method of claim 14, wherein said target binding moiety of the tagged probes further comprises a capture ligand having specific binding activity for a capture agent.

16. The method of claim 14, further comprising binding a set of tagged probes with a capture agent.

17. The method of claim 15, further comprising the step of separating one or more cleaved tagged probes from un-cleaved or partially cleaved tagged probes.

18. The method of claim 14, wherein said capture ligand further comprises biotin or an antigen.

19. The method of claim 14, wherein said capture agent is selected from the group consisting of avidin, streptavidin, an antibody, a receptor, or a functional fragment thereof, having specific binding affinity to the capture ligand.

* * * * *